US011478643B2

(12) United States Patent
Verzal et al.

(10) Patent No.: US 11,478,643 B2
(45) Date of Patent: Oct. 25, 2022

(54) POWER ELEMENT FOR AN IMPLANTABLE MEDICAL DEVICE

(71) Applicant: INSPIRE MEDICAL SYSTEMS, INC., Golden Valley, MN (US)

(72) Inventors: Kevin Verzal, Golden Valley, MN (US); Dave Dieken, Golden Valley, MN (US); John Rondoni, Golden Valley, MN (US)

(73) Assignee: INSPIRE MEDICAL SYSTEMS, INC., Golden Valley, MN (US)

( * ) Notice: Subject to any disclaimer, the term of this patent is extended or adjusted under 35 U.S.C. 154(b) by 365 days.

(21) Appl. No.: 16/471,859

(22) PCT Filed: Jan. 10, 2018

(86) PCT No.: PCT/US2018/013076
§ 371 (c)(1),
(2) Date: Jun. 20, 2019

(87) PCT Pub. No.: WO2018/132412
PCT Pub. Date: Jul. 19, 2018

(65) Prior Publication Data
US 2020/0086117 A1 Mar. 19, 2020

Related U.S. Application Data

(60) Provisional application No. 62/444,449, filed on Jan. 10, 2017.

(51) Int. Cl.
*A61N 1/37* (2006.01)
*A61N 1/36* (2006.01)
(Continued)

(52) U.S. Cl.
CPC ............ *A61N 1/3611* (2013.01); *A61N 1/378* (2013.01); *A61N 1/3756* (2013.01)

(58) Field of Classification Search
CPC ............................ A61N 1/3611; A61N 1/3756
(Continued)

(56) References Cited

U.S. PATENT DOCUMENTS 3,807,411 A 4/1974 Harris et al.
4,119,103 A 10/1978 Jirak
(Continued)

FOREIGN PATENT DOCUMENTS

JP 2001-511409 A 8/2001
JP 2006-507096 A 3/2006
(Continued)

OTHER PUBLICATIONS

Boston Scientific, Precision Spectra™ System Implantable Pulse Generator, Directions for Use, 2015, 18 pages.
(Continued)

*Primary Examiner* — Nicole F Lavert
(74) *Attorney, Agent, or Firm* — Dicke, Billig & Czaja, PLLC

(57) ABSTRACT

A power element for an implantable medical device is described. The implantable medical device includes sealingly contained circuitry and a sealingly contained power element. The sealingly contained power element supplies power to the circuitry.

17 Claims, 15 Drawing Sheets

(51) Int. Cl.
*A61N 1/375* (2006.01)
*A61N 1/378* (2006.01)

(58) Field of Classification Search
USPC .......................................................... 607/42
See application file for complete search history.

(56) References Cited

U.S. PATENT DOCUMENTS

| | | | |
|---|---|---|---|
| 5,314,451 A | 5/1994 | Mulier | |
| 5,411,538 A | 5/1995 | Lin | |
| 5,906,634 A | 5/1999 | Flynn et al. | |
| 6,067,474 A | 5/2000 | Schulman et al. | |
| 6,269,266 B1 | 7/2001 | Leysieffer | |
| 6,899,976 B2 | 5/2005 | Larson et al. | |
| 7,263,401 B2* | 8/2007 | Scott | A61N 1/37514 607/116 |
| 7,383,085 B2 | 6/2008 | Olson | |
| 7,442,465 B2 | 10/2008 | Kim et al. | |
| 7,640,061 B2 | 12/2009 | He et al. | |
| 7,881,796 B2 | 2/2011 | Scott et al. | |
| 8,359,098 B2 | 1/2013 | Lund et al. | |
| 8,433,409 B2 | 4/2013 | Johnson et al. | |
| 8,666,497 B2 | 3/2014 | Janzig et al. | |
| 8,670,823 B2 | 3/2014 | Murtonen | |
| 9,002,470 B2 | 4/2015 | Reinke et al. | |
| 9,216,285 B1 | 12/2015 | Boling et al. | |
| 9,220,911 B2 | 12/2015 | Gordon et al. | |
| 9,398,901 B2 | 7/2016 | Tischendorf et al. | |
| 2003/0171783 A1 | 9/2003 | Tsukamoto et al. | |
| 2004/0153127 A1 | 8/2004 | Gordon et al. | |
| 2004/0185337 A1 | 9/2004 | Ishizaki | |
| 2005/0004618 A1* | 1/2005 | Scott | A61N 1/37514 607/45 |
| 2005/0021100 A1 | 1/2005 | Tsukamoto et al. | |
| 2005/0021108 A1 | 1/2005 | Klosterman et al. | |
| 2007/0112404 A1 | 5/2007 | Mann et al. | |
| 2007/0150020 A1 | 6/2007 | Hokanson et al. | |
| 2007/0179581 A1 | 8/2007 | Dennis et al. | |
| 2007/0288077 A1 | 12/2007 | Bulkes et al. | |
| 2008/0109044 A1 | 5/2008 | Gramse et al. | |
| 2013/0085537 A1 | 4/2013 | Mashiach | |
| 2013/0245710 A1* | 9/2013 | Foster | A61N 1/3752 607/37 |
| 2015/0073247 A1* | 3/2015 | Gordon | A61N 1/3756 600/374 |
| 2016/0325105 A1 | 11/2016 | Etzkorn et al. | |
| 2018/0078775 A1 | 3/2018 | Linder et al. | |
| 2020/0147377 A1 | 5/2020 | Hoffer | |

FOREIGN PATENT DOCUMENTS

| | | |
|---|---|---|
| JP | 2012-510871 A | 5/2012 |
| JP | 5107783 B2 | 12/2012 |
| WO | WO2007059343 | 5/2007 |
| WO | 2010/065761 A2 | 6/2010 |
| WO | 2016/131492 A1 | 8/2016 |

OTHER PUBLICATIONS

Bal Seal Engineering Inc., Next-Generation IPGs Integrate Connector System Components, Sep. 17, 2014, 3 pages.
Bal Seal Engineering Inc., The Technologies behind the Next Generation of Neuromodulation Devices, May 3, 2016, 3 pages.
International Search Report, PCT/US2018/013076, dated Apr. 23, 2018, 16 pages.

* cited by examiner

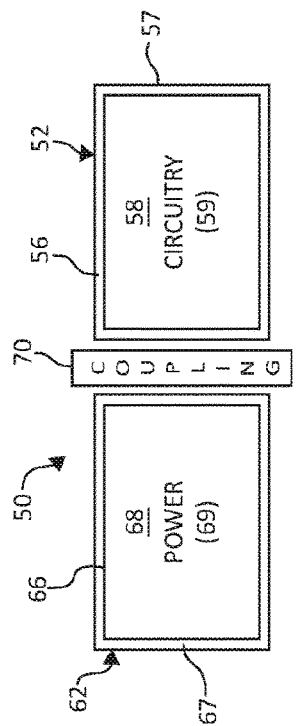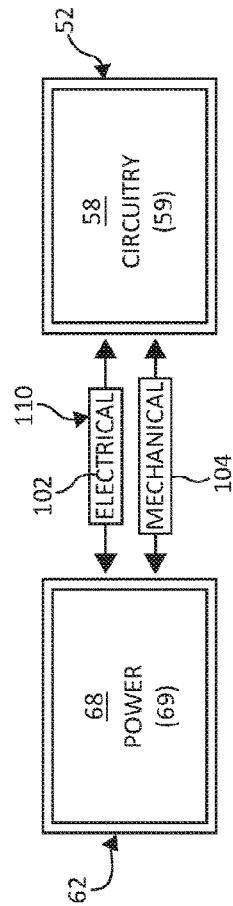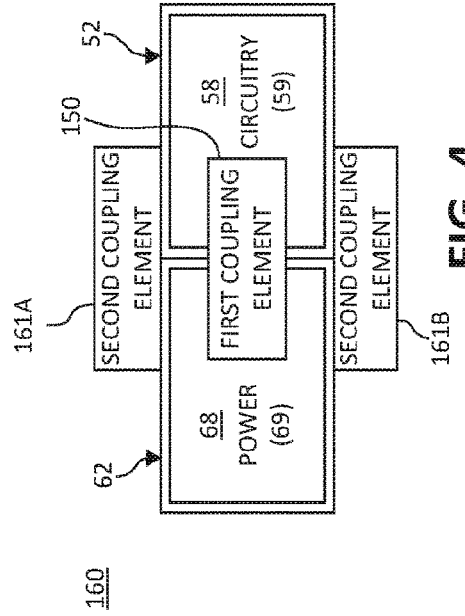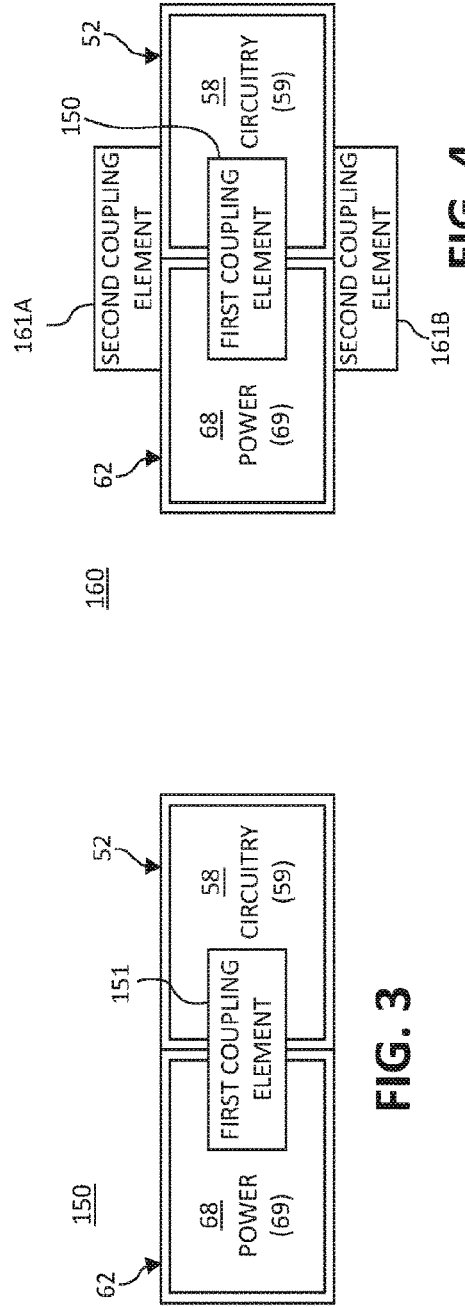

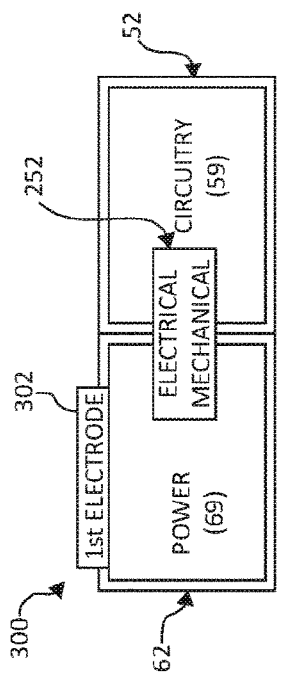
FIG. 8
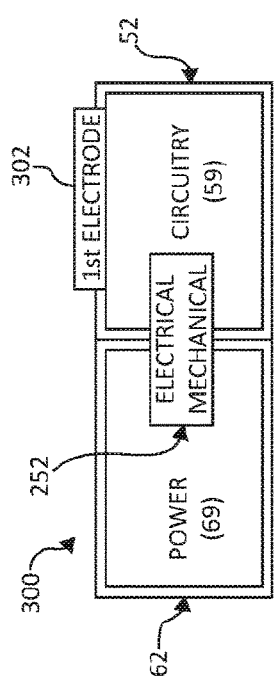
FIG. 9
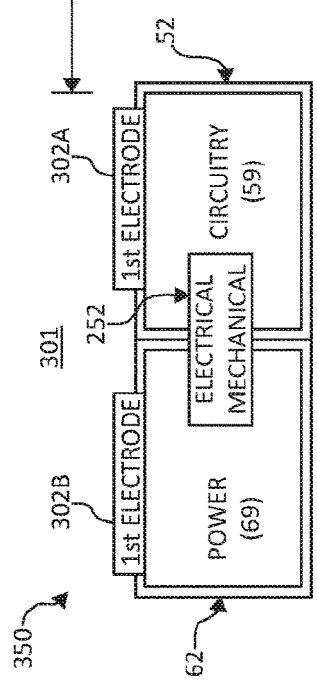
FIG. 10
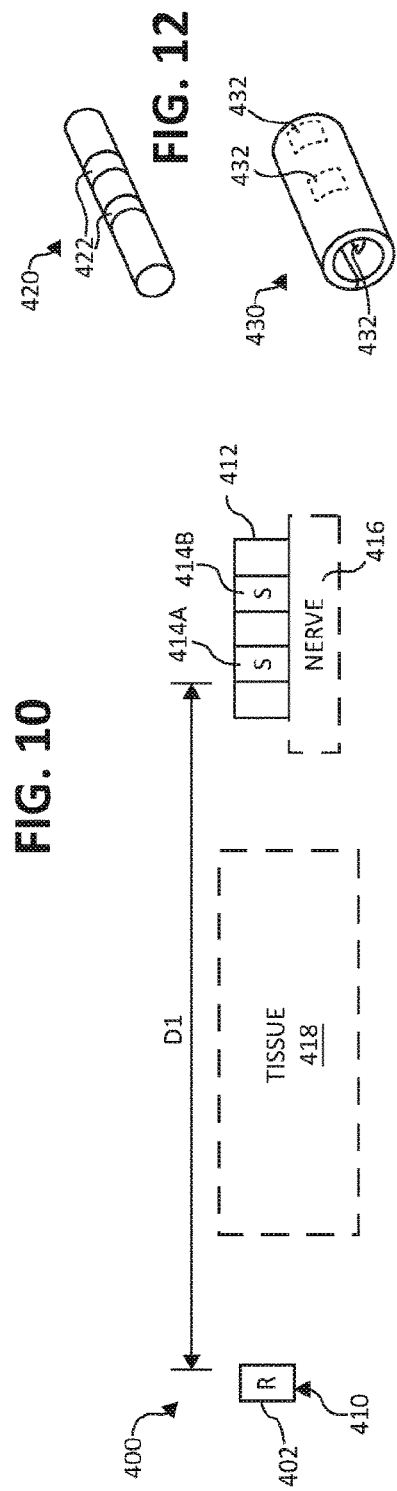
FIG. 11
FIG. 12
FIG. 13

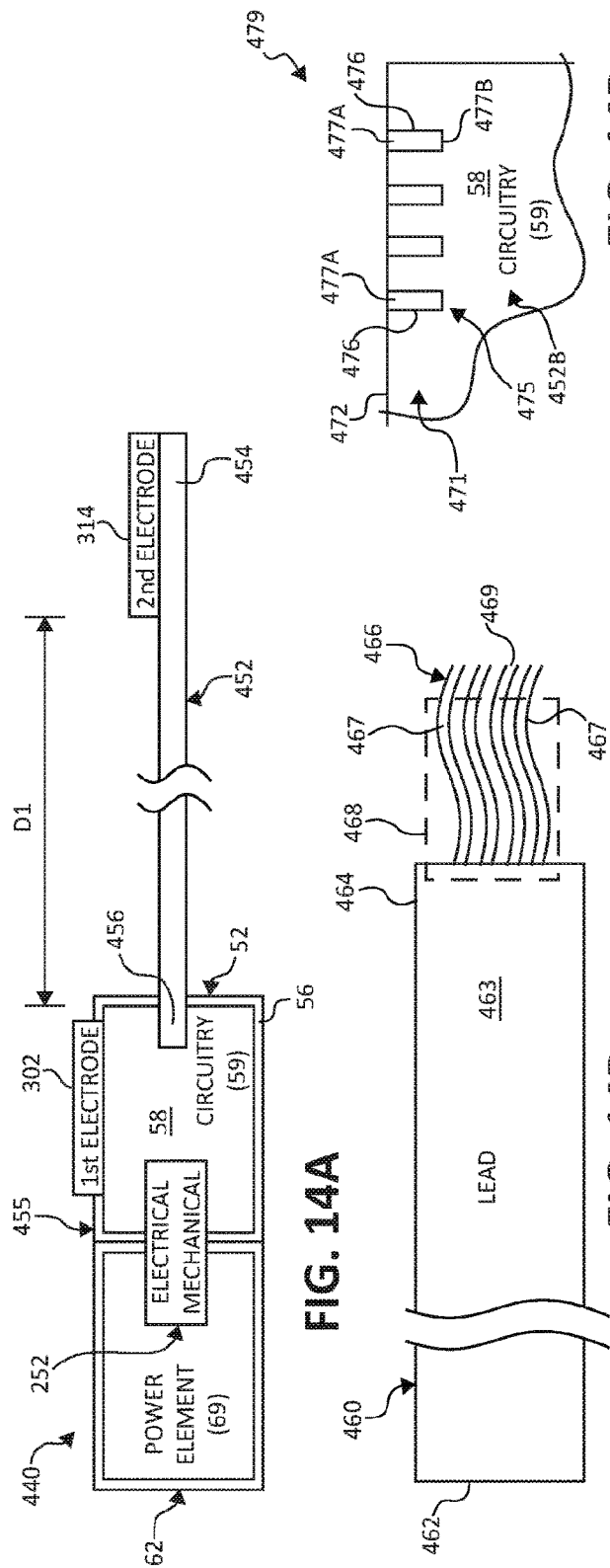

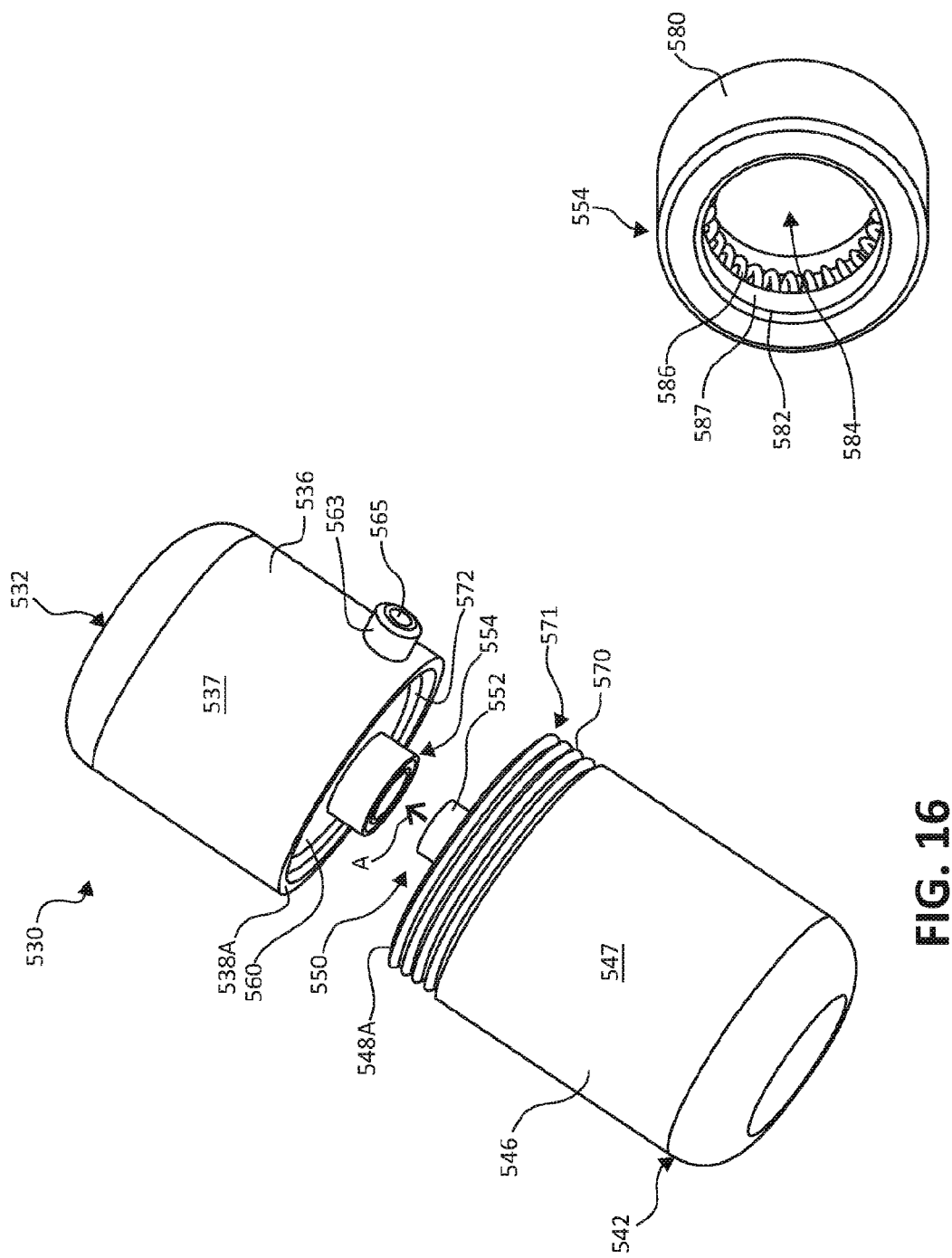

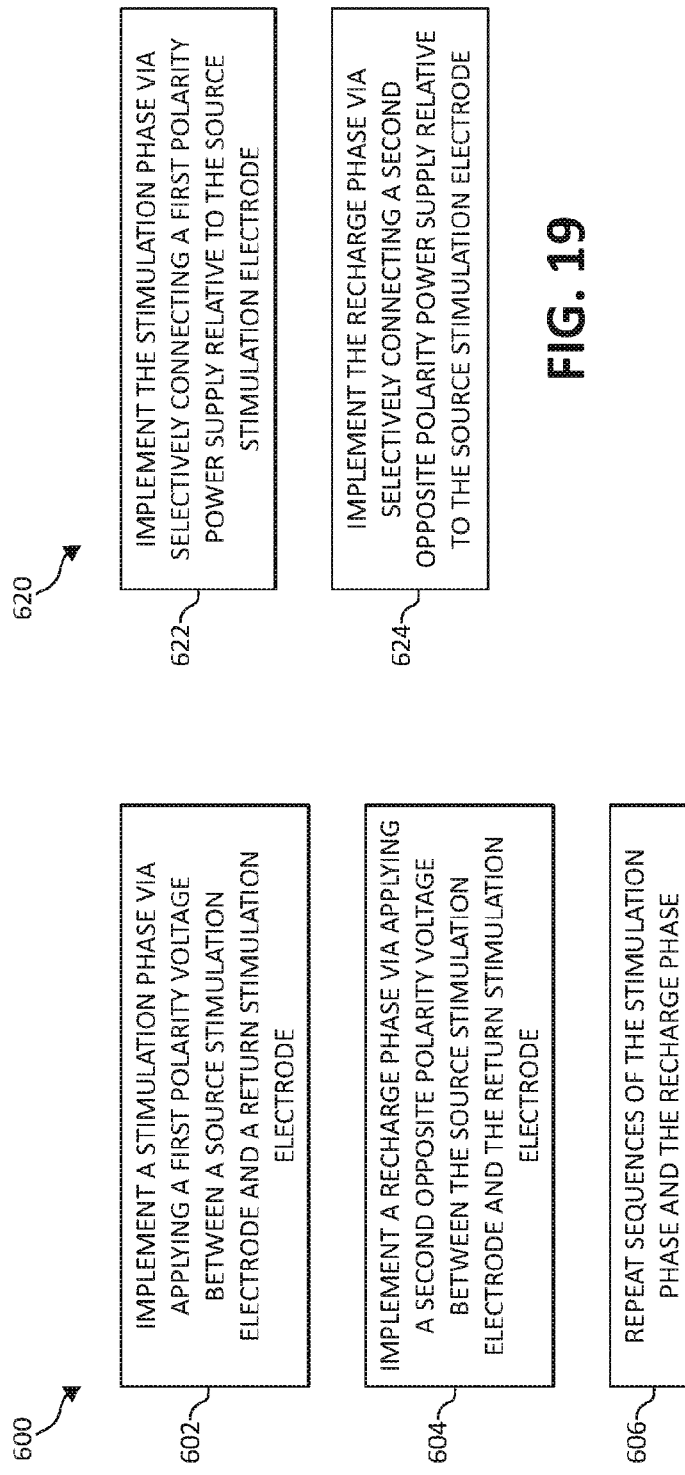

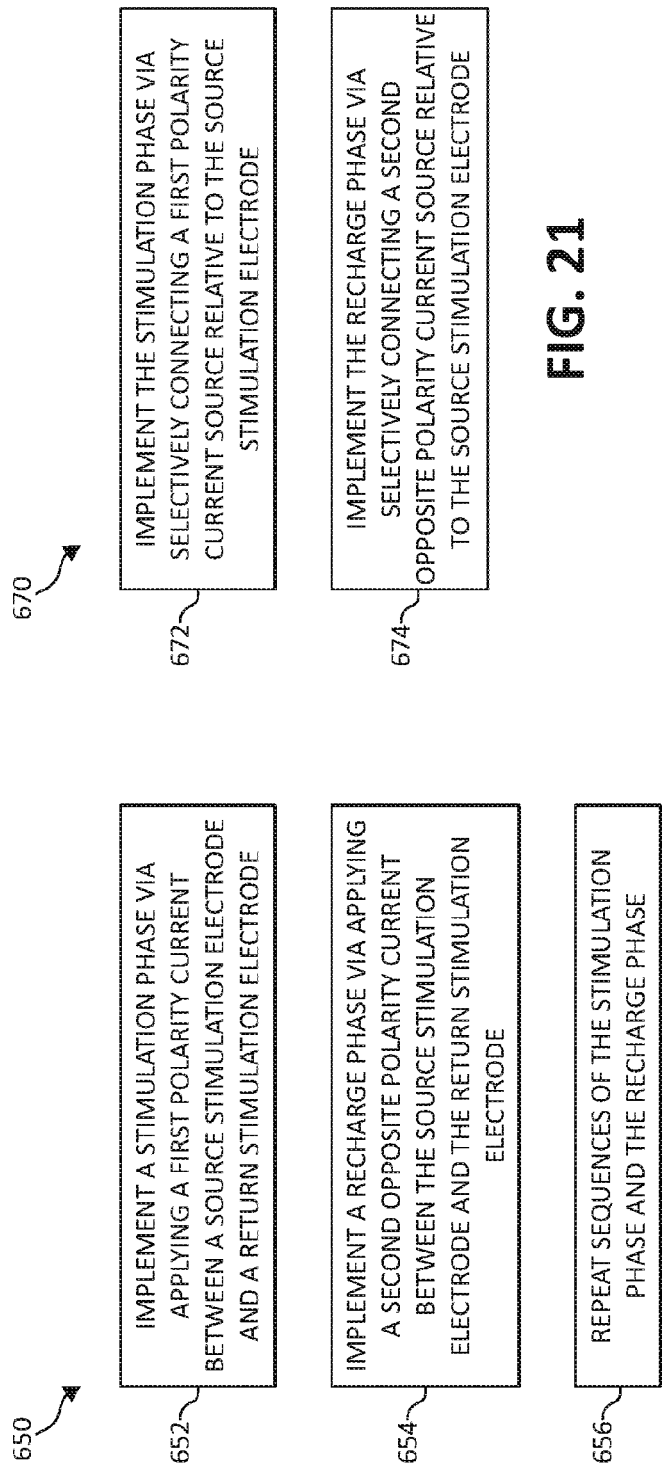

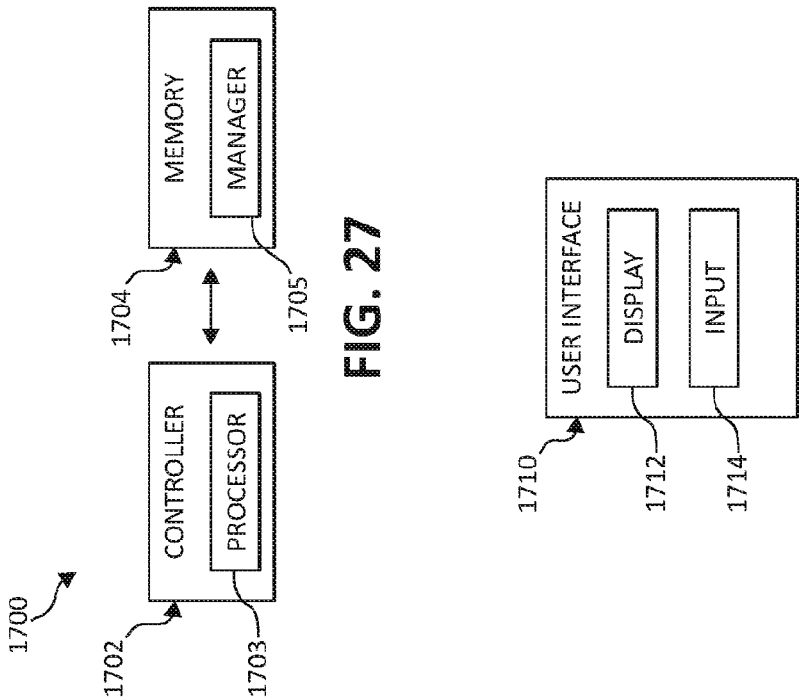
FIG. 27
FIG. 28
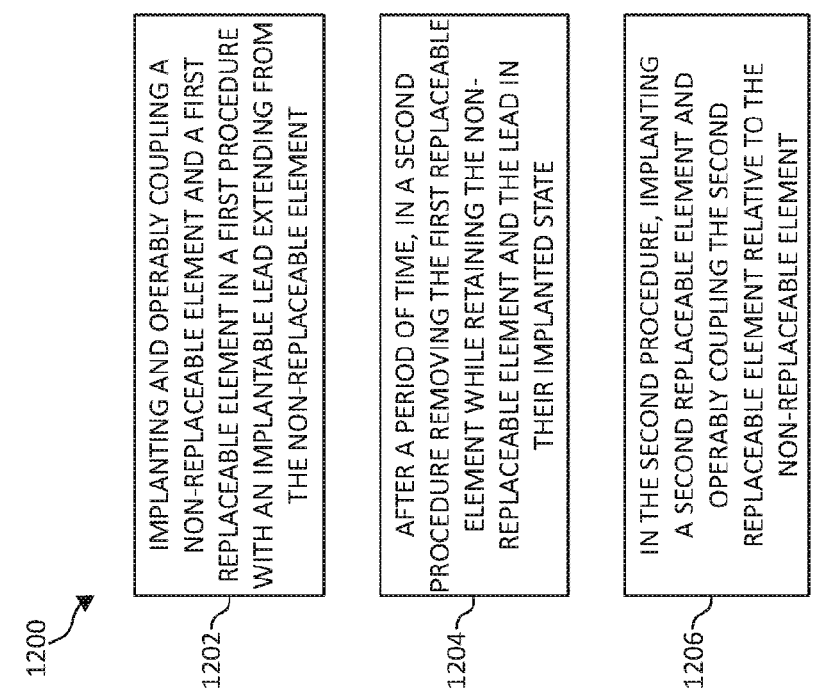
FIG. 26

POWER ELEMENT FOR AN IMPLANTABLE MEDICAL DEVICE

CROSS-REFERENCE TO RELATED APPLICATIONS

This 35 U.S.C. § 371 National Phase application claims priority to International Application No. PCT/US18/13076, filed Jan. 10, 2018, which claims the benefit of U.S. Provisional Patent Application No. 62/444,449, filed Jan. 10, 2017; which are both incorporated herein by reference in their entirety.

BACKGROUND

Treating sleep disordered breathing has led to improved sleep quality for some patients.

BRIEF DESCRIPTION OF THE DRAWINGS

FIG. 1 is a block diagram schematically representing an implantable medical device including a power element and a circuitry element operably coupled relative to each other, according to one example of the present disclosure.

FIG. 2 is a block diagram schematically representing an implantable medical device including a power element and a circuitry element coupled relative to each other electrically and/or mechanically, according to one example of the present disclosure.

FIG. 3 is a block diagram schematically representing an implantable medical device including a power element and a circuitry element coupled relative to each other via a first coupling element, according to one example of the present disclosure.

FIG. 4 is a block diagram schematically representing an implantable medical device including a power element and a circuitry element coupled relative to each other via a first coupling element and a second coupling element, according to one example of the present disclosure.

FIG. 8 is a block diagram schematically representing an implantable medical device including an electrode on a housing associated with a circuitry element, according to one example of the present disclosure.

FIG. 9 is a block diagram schematically representing an implantable medical device including an electrode on a housing associated with a power element, according to one example of the present disclosure.

FIG. 10 is a block diagram schematically representing an implantable medical device including an electrode array including a second electrode and first electrodes on a housing respectively associated with a circuitry element and/or a power element, according to one example of the present disclosure.

FIG. 11 is a block diagram schematically representing a stimulation electrode array associated with an implantable medical device including a return stimulation electrode and at least one source stimulation electrode, according to one example of the present disclosure.

FIG. 12 is an isometric view schematically representing an electrode portion of a stimulation element including an electrode array, according to one example of the present disclosure.

FIG. 13 is an isometric view schematically representing a cuff electrode of a lead including an electrode array, according to one example of the present disclosure.

FIG. 14A is a block diagram schematically representing an implantable medical device including a stimulation electrode array arranged relative to a lead and a housing of a pulse generator, according to one example of the present disclosure.

FIG. 14B is a side plan view schematically representing a lead, according to one example of the present disclosure.

FIG. 14C is a partial side view schematically representing a connection portion of an implantable element including circuitry, according to one example of the present disclosure.

FIG. 14D is a partial side view schematically representing a connection portion of an implantable element, according to one example of the present disclosure.

FIG. 14E is an isometric view schematically representing a connection portion of an implantable element, according to one example of the present disclosure.

FIG. 16 is an isometric view schematically representing removable connection of housing portions of an implantable medical device, according to one example of the present disclosure.

FIG. 17 is an isometric view schematically representing at least a portion of a coupling element associated with housing portions of an implantable medical device, according to one example of the present disclosure.

FIG. 18 is a flow diagram schematically representing a method of voltage mode stimulation, according to one example of the present disclosure.

FIG. 19 is a flow diagram schematically representing aspects associated with a method of voltage mode stimulation, according to one example of the present disclosure.

FIG. 20 is a flow diagram schematically representing a method of current mode stimulation, according to one example of the present disclosure.

FIG. 21 is a flow diagram schematically representing aspects associated with a method of current mode stimulation, according to one example of the present disclosure.

FIG. 26 is a flow diagram schematically representing a method of replacing an implanted element associated with an implantable medical device, according to one example of the present disclosure.

FIG. 27 is a block diagram schematically representing a control portion, according to one example of the present disclosure.

FIG. 28 is a block diagram schematically representing a user interface, according to one example of the present disclosure.

DETAILED DESCRIPTION

Figure 6:
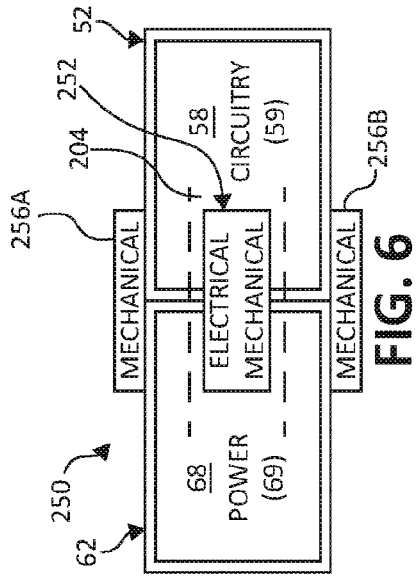
FIG. 6 is a block diagram schematically representing an implantable medical device including a power element and a circuitry element coupled relative to each other electrically and mechanically, according to one example of the present disclosure.

In the following Detailed Description, reference is made to the accompanying drawings which form a part hereof, and in which is shown by way of illustration specific examples of the present disclosure which may be practiced. In this regard, directional terminology, such as "top," "bottom," "front," "back," "leading," "trailing," etc., may be used with reference to the orientation of the Figure(s) being described. Because components of at least some examples of the present disclosure can be positioned in a number of different orientations, the directional terminology is used for purposes of illustration and is in no way limiting. It is to be understood that other examples may be utilized and structural or logical changes may be made without departing from the scope of the present disclosure. The following detailed description, therefore, is not to be taken in a limiting sense. It is to be understood that features of the various examples described herein may be combined, in part or whole, with each other, unless specifically noted otherwise.

In at least some examples of the present disclosure, a power element is associated with an implantable medical device (IMD). In some examples, the implantable medical device (IMD) comprises an implantable neurostimulator, which may comprise an implantable pulse generator (IPG) and associated components. However, in some examples, the implantable medical device (IMD) may additionally comprise or alternatively comprise implantable monitoring functionality (e.g. monitoring elements, circuitry, and/or stored instructions, etc.), which may or may not include sensing functionality, such as receiving sensed signals, sensors, related stored instructions, etc.

In some examples, the power element is operably couplable relative to a circuitry element of the implantable medical device. In some examples, the circuitry element is sealingly contained within a first housing portion and the power element is sealingly contained in a second housing portion, and as such the power element is sealingly contained separate from, and independent of, the circuitry element. In some examples, the second housing portion defines a single outer wall which sealingly contains power components (e.g. battery) with the outer wall being directly exposable to tissue within the patient's body.

Via at least some such examples, the power element occupies space within its own housing and as such, the power element does not occupy or share space within a housing containing circuitry configured to produce nerve stimulation signals.

Accordingly, at least some examples of the present disclosure avoid arrangements which sealingly contain both a power element and a circuitry element (e.g. for nerve stimulation) within a single housing (e.g. the same housing). Such arrangements typically are more expensive and have a larger volume, which occupies more space within a patient's body. For instance, this increased cost and larger volume may result from having to include infrastructure within the single housing to stabilize and secure the battery within and relative to the shell or casing of the single housing. In some instances of commercially available devices, such infrastructure may be significant due to the relatively high weight of the battery relative to the weight of the circuitry portion and/or due to the presence of other components within the single housing.

Similarly, such commercially available arrangements typically include insulation surrounding the battery within the single housing to thereby electrically isolate the battery (within the single housing) from the conductive shell or casing of the single housing. In some such arrangements, besides a pair of electrical connections between the circuitry portion and the power portion (e.g. battery), additional connections are present such as an electrical connection between the circuitry and the shell or casing of the single housing.

In sharp contrast to such arrangements, via at least some of the previously described examples of the present disclosure, an implantable medical device includes a power element which is sealingly contained separately from a circuitry element to which the power element may provide power. As further detailed herein, such examples may result in a smaller, simpler, and/or less expensive implantable medical devices. In addition, such examples may result in new, different opportunities for deploying a stimulation electrode array.

With this in mind, in some examples, at least a portion of the outer wall of the second housing portion (which sealingly contains power components) includes an electrode. In some examples, this electrode forms part of a stimulation electrode array and may function as a return stimulation electrode relative to at least one source stimulation electrode spaced apart from the return electrode, with tissue present in the intervening space between the at least one source stimulation electrode and the return stimulation electrode.

In some examples, the at least one source stimulation electrode is external to and separate from the power element and/or circuitry element of the implantable medical device.

In some such examples, the at least one source stimulation electrode is located on a portion of a lead extending from the pulse generator. Via implantation of the lead in an appropriate portion of the patient's body, the at least one source stimulation electrode is placed adjacent to or against a nerve to permit application of a nerve stimulation signal via the electrode array. In some examples, the nerve comprises a nerve innervating muscles (e.g. upper airway muscles) related to restoring airway patency. In some examples, the nerve comprises the hypoglossal nerve (and/or other nerves) and associated muscles (e.g. genioglossus muscle) responsible for causing movement of the tongue and related musculature to restore airway patency. Via at least some of such examples, the stimulation electrode array may be employed to treat sleep disordered breathing (SDB), such as apneas. Such apneas may include, but are not limited to, obstructive sleep apnea. In some examples, stimulation circuitry can generate electrical signals deliverable through a stimulation element suitable for exciting a target nerve associated with muscles that can restore airway patency.

Meanwhile, in some examples the return stimulation electrode is located on an implantable pulse generator (IPG). In some examples, the return stimulation electrode is located on the second housing portion (sealingly containing power components) of the pulse generator. In some such examples, the return stimulation electrode located on the second housing portion (e.g. the housing of the power element) defines both an external surface of the second housing portion and an exterior wall of the power element. In some such examples, the exterior wall of the power element is exposable directly to tissue within a patient's body when the implantable medical device is in its implanted position within the body. Stated differently, in at least some examples a power element (e.g. a battery) may comprise an external case which comprises a return electrode, defines a housing for the battery, and is directly exposable to surrounding tissue.

In some examples, the at least one source stimulation electrode may be implemented as a cathode while the return stimulation electrode may be implemented as an anode.

In some examples, the power element provides power to the circuitry element in a non-floating architecture. Stated differently, as noted above the power components (e.g. battery) sealingly contained via the second housing portion are not electrically isolated from the conductive shell or casing defining the outer wall of the second housing portion. Instead, one of the negative pole and the positive pole of the power element define a case of the power element, which is directly exposable to the bodily tissues within the patient. In contrast, in a floating battery architecture, both the negative and positive poles of the battery are electrically isolated from a case (e.g. implantable pulse generator) in which they are enclosed.

Via such at least some such example arrangements, nerve stimulation may be applied via a voltage mode or a current mode. In the voltage mode, a first polarity voltage and then a second opposite polarity voltage is applied between the at least one source stimulation electrode and the return stimulation electrode with this sequence being repeated in cycles. In the current mode, a first polarity current and then a second opposite polarity current is applied between the at least one source stimulation electrode and the return electrode with this sequence being repeated in cycles. In some examples, the first polarity is negative and the second opposite polarity is positive.

As previously noted, in some examples the circuitry element is sealingly contained within the first housing portion and the power element is sealingly contained in the second housing portion, and as such the power element is sealingly contained separate from, and independent of, the circuitry element. In some of these examples, the power element may be permanently connected (electrically and mechanically) to the circuitry element. However, in some of these examples, the power element may be removably connectable (electrically and mechanically) relative to the circuitry element. Having a removably connectable power element may enable an operator to select, prior to implantation, from among differently sized power elements, and thereby select from among different power capacities. In some examples, having a removably connectable power element may enable later replacement of the power element after implantation with the circuitry element (and any associated leads connected thereto) remaining in their implanted position within the patient's body.

These examples, and additional examples, are described in more detail in association with at least FIGS. 1-29.

FIG. 1 is a block diagram schematically representing an implantable medical device (IMD) 50, according to one example of the present disclosure. As shown in FIG. 1, in some examples, IMD 50 comprises a circuitry element 52 and a power element 62 to supply power to the circuitry element 52.

It will be understood that the term "device" as used in the present disclosure may comprise several components working in cooperation whether such components are permanently connected, removably connected, or permanently separate from each other. Accordingly, in some examples a device may comprise a singular unitary piece (i.e. monolithic) having a single portion or multiple portions (e.g. power, circuitry, lead). In some examples, a device may comprise an arrangement of multiple separable pieces (e.g. power, circuitry, lead) which function in a complementary manner.

In some examples, the power element 62 sealingly contains a power source 69 within an interior 68. The power source 69 which may be a battery (one or several) or other rechargeable power component. In some such examples, the power element 62 includes an exterior wall 66 which also defines a housing to sealingly contain the power source (e.g. energy source). In some such examples, the external surface 67 of wall 66 of power element 62 is directly exposable to tissue within the patient's body. As such, there is no second wall outside of the wall 66. In some examples, the entire wall 66 and/or at least its external surface 67 is made of a biocompatible material and/or is coated with biocompatible material. In some examples, the biocompatible material may be electrically conductive, which may in some instances enable the external surface to provide power and/or circuitry functionality in relation to a stimulation electrode array or related components. However, in some examples, the biocompatible material may be electrically insulative.

In some examples, portions of the biocompatible materials are electrically conductive and portions of the biocompatible materials are electrically insulative. In other words, a portion of external surface 67 may exhibit electrically conductive behavior while other portions of external surface 67 may exhibit electrically insulative behavior. In some examples, the electrically insulative behavior may be implemented via coatings such as parylene, silicone, etc.

Power element 62 may take a wide variety of sizes and/or shapes (e.g. cylindrical, cubic, thin disc, rectangular, etc.). Accordingly, it will be understood that the power element 62 is not strictly limited to the generally rectangular shape in FIG. 1 and to other shapes (e.g. FIG. 16) shown throughout the examples of the present disclosure.

In some examples, the circuitry element 52 of the implantable medical device 50 is sealingly contained, such as being hermetically sealed. The circuitry element 52 sealingly contains circuitry 59 within an interior 58. The circuitry 59 may include circuitry to implement neurostimulation and/or monitoring functions. In some examples, the circuitry 59 may comprise an application specific integrated circuit (ASIC). In some such examples, the circuitry element 52 includes an exterior wall 56 which also defines a housing to sealingly contain circuitry components. In some such examples, the external surface 57 of wall 56 of circuitry element 52 is directly exposable to tissue within the patient's body.

In some examples, the power element 62 and circuitry element 52 are operably coupled relative to each other as represented via coupling 70.

In some examples, the power element 62 and the circuitry element 52 are selectively operably coupled relative to each other such that the power element 62 may selectively provide power to the circuitry element 52 when the power element 62 and circuitry element 52 are coupled together. In other words, via a removable connection, the power element 62 and circuitry element 52 may be operably coupled or may be separated. In examples in which they are separable, the power element 62 and the circuitry element 52 may sometimes be referred to as being coupled in a weld-free manner.

FIG. 2 is a block diagram schematically representing an implantable medical device 100, according to one example of the present disclosure, and comprising at least some of substantially the same features and attributes as implantable medical device 50 in FIG. 1. As shown in FIG. 2, in at least some examples the operable coupling 70 in FIG. 1 may be implemented as operable coupling 110 by which the power element 62 and circuitry element 52 may be electrically connectable 102 and/or mechanically connectable 104 relative to each other.

FIG. 3 is a block diagram schematically representing an implantable medical device 150, according to one example of the present disclosure, and comprising at least some of substantially the same features and attributes as implantable medical device 50, 100 in FIGS. 1-2. As shown in FIG. 3, in some examples, an implantable medical device 150 comprises a first coupling element 151 to operably couple the power element 62 and the circuitry element 52 relative to each other. While in some examples, the first coupling element 151 may be located centrally as shown in FIG. 3, in some examples, the first coupling element 151 may be located non-centrally and may have other shapes and/or sizes than shown in FIG. 3.

The first coupling element 151 may comprise mechanical component(s) (e.g. 104 in FIG. 2) to mechanically secure at least a housing of the power element 62 and a housing of the circuitry element 52 relative to each other. In some examples, via the first coupling element 151, the power element 62 and the circuitry element 52 are permanently secured relative to each other. In some examples, via such operable coupling, power components within a housing of the power element 62 and circuitry components within a housing of the circuitry element 52 are electrically connected (e.g. 102 in FIG. 2) to each other. In some examples, the different electrical connections 102 and mechanical connections 104 of such operable coupling via element 151 are further schematically represented in at least FIG. 5 for the example implantable medical device 200.

FIG. 4 is a block diagram schematically representing an implantable medical device 160, according to one example of the present disclosure, and comprising at least some of substantially the same features and attributes as implantable medical device 50, 100, 150 in FIGS. 1-3. As shown in FIG. 4, in addition to having a first coupling element 151 as in FIG. 3, in some examples an implantable medical device 160 comprises a second coupling element 161A, 161B which further operably couples the power element 62 and the circuitry element 52 relative to each other.

FIG. 6 is a block diagram schematically representing an implantable medical device 250, according to one example of the present disclosure, and comprising at least some of substantially the same features and attributes as implantable medical device 50, 100, 160 in FIGS. 1-4. As shown in FIG. 6, implantable medical device 250 comprises electrical-mechanical connection elements 252 connecting the respective power and circuitry elements 62, 52. In some examples the second coupling element 161A, 161B shown in FIG. 4 for implantable medical device 160 comprises solely a mechanical coupling 256A, 256B in the implantable medical device 250 of FIG. 6. In some examples, the mechanical coupling 256A, 256B may be implemented in a manner such that the exterior wall of the housing of power element 62 is electrically isolated from the exterior wall of the housing of circuitry element 52.

Figure 7:
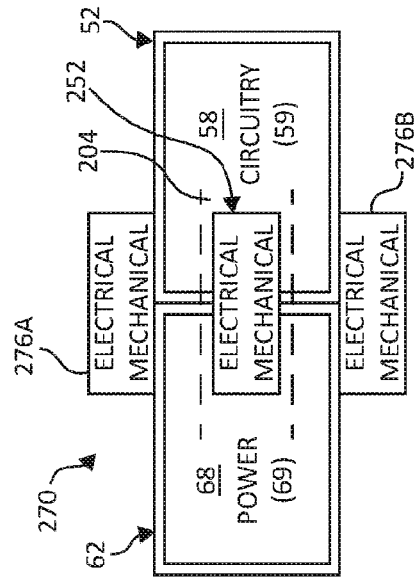
FIG. 7 is a block diagram schematically representing an implantable medical device including a power element and a circuitry element coupled relative to each other electrically and mechanically, according to one example of the present disclosure.

FIG. 7 is a block diagram schematically representing an implantable medical device 270, according to one example of the present disclosure, and comprising at least some of substantially the same features and attributes as implantable medical device 50, 100, 160 in FIGS. 1-4. As shown in FIG. 7, in some examples when implemented in implantable medical device 270, the second coupling element 161A, 161B (FIG. 4) comprises both electrical and mechanical connection elements coupling 276A, 276B, such that the housing of the power element 62 is electrically connected to, and electrically common with, the housing of the circuitry element 52.

Figure 5:
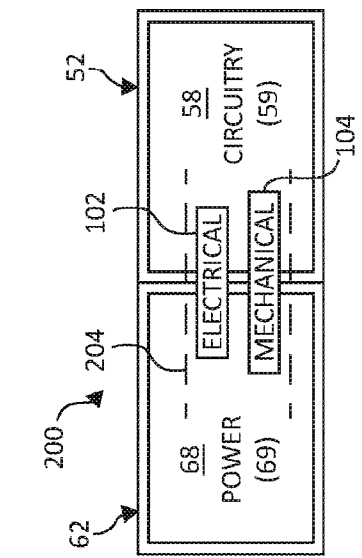
FIG. 5 is a block diagram schematically representing an implantable medical device including a power element and a circuitry element coupled relative to each other electrically and mechanically via a feedthrough, according to one example of the present disclosure.

In some examples, as shown via the dashed lines 204 in each of the different example implantable medical devices in FIGS. 5-7, the electrical and mechanical connection elements of the operable coupling may be implemented as a single feedthrough 204. In some examples, a feedthrough 204 comprises a conductive element from an interior 68 of one element (e.g. the power element 62) into an interior 58 of another element (e.g. the circuitry element 52) for direct connectability of power components in power element 62 relative to circuitry components in circuitry element 52.

As shown in FIGS. 8-10, in some examples an implantable medical device (IMD) 300, 350 comprises at least some of substantially the same features and attributes as the IMD previously described in association with at least FIGS. 1-7, except further comprising an electrode 302 on a housing of the power element 62 (FIG. 8) or of the circuitry element 52 (FIG. 9), or except further comprising an electrode 302A, 302B located on a housing of each of the power element 62 and the circuitry element 52 of an IMD 350, as shown in FIG. 10.

As further shown in FIG. 10, in some examples, the electrode 302 in FIGS. 8-9 or the electrode 302A, 302B in FIG. 10 may comprise part of a stimulation electrode array 310, which further comprises at least one second electrode 314 spaced apart by a distance (D1) from the first electrode 302A (or 302B). It will be further understood that in some examples in which the housing of the power element 62 is electrically connected to the housing of the circuitry element 52, one electrode 302 on the housing of either the power element 62 or the circuitry element 52 would be common to both housings.

In some examples, the stimulation electrode array 310 of IMD 350 in FIG. 10 (or for IMD 300 in FIG. 8 or 9) may be further represented by the example arrangement 400 in FIG. 11 in which a stimulation electrode array 410 comprises a return stimulation electrode 402 (e.g. first electrode 302A, 302B in FIG. 10 or 302 in FIGS. 8-9) and at least one source stimulation electrode 414A, 414B (e.g. second electrode 314 in FIG. 10). As shown in FIG. 11, intervening tissue 418 is located between the at least one source stimulation electrode 414A, 414B and the return stimulation electrode 402, which are spaced apart by a distance D1. The source electrodes 414A, 414B are operably couplable relative to a nerve 416 to be stimulated. However, in some examples, it will be understood that the source stimulation electrodes 414A, 414B may be operably coupled relative to a muscle to be stimulated.

In some examples, nerve 416 comprises a nerve related to upper-airway-patency such that stimulation of the nerve may contribute to or result in restoring or maintaining upper-airway patency. In some examples, such stimulation may contribute to treatment of sleep disordered breathing (SDB), such as but not limited to, obstructive sleep apnea (OSA) and/or other types of apneic behavior.

In some examples, the spacing D1 is sufficiently large that the source stimulation electrodes 414A, 414B are in one portion of the body (e.g. head and neck region) and the return stimulation electrode 402 is in another portion of the body (e.g. pectoral region), such as may be observed later in FIG. 29 in which a stimulation electrode is in the head-and-neck region while the implantable medical device (e.g. an IPG) is in the pectoral region. However, in some examples, a lesser spacing D1 may permit the stimulation electrodes 414A, 414B to be located in the same portion of the body (e.g. head and neck region) as the return stimulation electrode 402. Further details regarding some potential arrangements are described in association with at least FIGS. 14A, 15C and/or FIG. 29.

In some examples, at least one of the source stimulation electrodes 414A, 414B, etc. may be implemented as a ring electrode 422 exposed on a stimulation element 420, as shown in FIG. 12 or may be implemented as electrodes 432 exposed within a cuff electrode 430, as shown in FIG. 13. In some examples, source stimulation electrodes 414A, 414B may be implemented within a cuff electrode having at least some of substantially the same features and attributes as one of the cuff electrodes described in Bonde et al. U.S. Pat. No. 9,227,053, "Self-Expanding Electrode Cuff", issued on Jan. 5, 2016, and in Bonde et al. U.S. Pat. No. 8,340,785, "Self-Expanding Electrode Cuff", issued on Dec. 25, 2012, both of which are herein incorporated by reference.

It will be understood that second stimulation electrodes 414A, 414B may be implemented in other configurations, shapes, etc. and with or without a lead interposed between the source stimulation electrodes 414A, 414B and the return stimulation electrode 402.

In some examples, at least one of the source stimulation electrode(s) 414A, 414B in FIG. 11 (or 314 in FIG. 10) is located on a housing of the circuitry element 52 or of the power element 62 to be spaced apart from the return stimulation electrode (e.g. 302, 302A, 302B). Accordingly, in at least some such examples, power element 62 and circuitry element 52 may be positioned in close proximity to a nerve to be stimulated to place the source stimulation electrode (e.g. 314, 414A, 414B) on the housing (of the circuitry element 52 or of power element 62) to enable stimulating the nerve.

FIG. 14A is a block diagram schematically representing an implantable medical device 440, according to one example of the present disclosure, and comprising at least some of substantially the same features and attributes as implantable medical device 50, 100, etc. in FIGS. 1-13. As shown in FIG. 14A, in some examples a stimulation electrode array (e.g. array 410 in FIG. 11 or 310 in FIG. 10) may be implemented in association with a lead 452 of an implantable medical device (IMD) 440. As shown in FIG. 14A, IMD 440 comprises a pulse generator 455 having at least some of substantially the same features and attributes of an implantable medical device having pulse generator functionality (e.g. circuitry, power, stored instructions, etc. to at least generate and apply stimulation pulses), as previously described in association with at least FIGS. 1-13, except further comprising lead 452 operably coupled relative to at least circuitry element 52 and supporting at least one second stimulation electrode 314 (e.g. source electrodes 414A, 414B in FIG. 11). The lead 452 comprises a distal portion 454 on which the at least one second stimulation electrode 314 is located, although the at least one second stimulation electrode 314 may be located along other non-distal portions of lead 452 in some examples. In some examples, lead 452 includes features and attributes at least consistent for use in an implantable stimulation system as described in U.S. Pat. No. 6,572,543 to Christopherson et al, which is hereby incorporated by reference.

In some examples, a proximal portion 456 of lead 452 is operably coupled relative to circuitry element 52. In some examples, such operable coupling is permanent. In some examples, such operable coupling comprises a proximal portion 456 of lead 452 being electrically connected to circuitry components within circuitry element 52 and being mechanically connected relative to circuitry element 52, whether such mechanical connection is implemented relative to interior 59 and/or exterior wall 56 of circuitry element 52.

In some examples, via such a permanent connection between a lead and an implantable pulse generator (IPG) (including power element and circuitry element), the circuitry element 52 sometimes may be implemented as a headerless IPG, because no header is used to removably connect leads to the circuitry element in this arrangement. In some examples, eliminating the header (e.g. connector block) may reduce the overall volume of the implantable pulse generator (e.g. including the power element and the circuitry element) of an implantable medical device by about 20 percent. In some examples, the overall volume may be reduced by up to 50 percent, or even more in some cases.

Such volume reduction may ease implantation while providing a less noticeable appearance on the patient's body. Moreover, in some examples, such volume reduction may increase the number and/or type of implantation locations that have been previously avoided due to a size of a pulse generator. In some examples, at least some features associated with a headerless IPG are further described later in association with at least FIGS. 14C-14D.

In some examples, part of the overall volume reduction for an implantable pulse generator achieved via a headerless configuration may involve reducing a "connection volume" (e.g. a volume involved in connecting a lead to the circuitry within pulse generator) by more than 50 percent. In some examples, this reduced connection volume may be more than 80 percent.

In some examples, a lead which is permanently connected to the circuitry element 52 may take the form schematically represented in FIG. 14B in which lead 460 comprises a body 463 extending between a distal end 462 and an opposite proximal end 464. At the proximal end 464, an array 466 of connection elements 467 extends for connection to circuitry via a corresponding array of feedthrough posts 476 or 486 as described in association with FIGS. 14C-14D, respectively. As further shown in FIG. 14B, in some examples the entire array 466 of connection elements 467 may be encapsulated in a non-conductive material as represented by dashed lines 468 with it being understood that each element 467 comprises an electrically non-conductive external surface or coating to electrically isolate the elements 467 from each other and the surrounding tissue.

FIG. 14C is partial side view schematically representing an implantable medical device (IMD) 470, according to one example of the present disclosure. The IMD 470 may comprise at least some of substantially the same features and attributes as IMD 440 (FIG. 14A) or as one of the other example implantable medical devices as previously described in association with FIGS. 1-13. As shown in FIG. 14C, a circuitry element 452A of the IMD 470 includes a housing 471 defining at least an external surface 472 in which is formed a recess 474. The IMD 470 comprises an array 475 of feedthrough posts 476 for connection to corresponding elements of a lead. As shown in FIG. 14C, each feedthrough post 476 comprises a distal end 477A and a proximal end 477B. With proximal end 477B connected to circuitry 59 within an interior 58 of circuitry element 452A, each post 476 has a length such that the distal end 477A protrudes out from a bottom portion 473A of recess 474 to be exposed for permanent connection to elements of a lead (e.g. FIG. 14B). The permanent connection may be implemented via welding, fastening mechanisms, etc. In some examples, the welding may be performed via direct welding techniques such as resistance welding, laser welding, etc.

In some examples, at least the surface area of the distal ends 477A of posts 476 may be larger (e.g. 50% more, 100% more) than the ends 469 of elements 467 (FIG. 14B) of lead 460 to provide a significant weld target area.

In some examples, after being welded together, the posts 476 and at least a portion of elements 467 of lead 460 are coated or encapsulated in an electrically non-conductive material, such as an epoxy, silicone adhesive, etc.

In this arrangement, as shown in FIG. 14C the distal ends 477A of posts 476 are located within the recess 474, and therefore do not extend externally to the external surface 472 of the general contour of housing 471 of circuitry element 452A. Accordingly, in some examples, a point of permanent connection between the elements 467 of lead 460 and the posts 476 occurs within (i.e. does not protrude beyond) the outermost external surface 472 of the general contour of housing 471 of circuitry element 452A.

In some examples, the dashed line 478 defines a boundary around an area 479 in which a header would otherwise be present in traditional designs, and as such provides a context by which one can better appreciate the space saved by the headerless design in the example of the present disclosure in FIGS. 14C-14E, and as at least partially described above.

FIG. 14D is a partial side view schematically representing an implantable medical device (IMD) 479, according to one example of the present disclosure. In some examples, IMD 479 comprises at least some of substantially the same features and attributes as previously described for IMD 470 (FIG. 14C) except having a circuitry element 452B with the external surface 472 of housing 471 completely omitting a recess 474 or including a minimal recess such that the ends 477A of posts 476 are flush or substantially flush with the external surface 472 of the general contour of the housing 471 of circuitry element 452B.

FIG. 14E is a partial perspective view schematically representing an implantable medical device (IMD) 480, according to one example of the present disclosure. In some examples, IMD 480 comprises at least some of substantially the same features and attributes as IMD 470 (FIG. 14C) except at least omitting a recess 474 within which posts 476 reside. Accordingly, in the IMD 480, via aperture 484 an array 485 of feedthrough posts 486 protrude from, and are exposed relative to, external surface 472 of circuitry element 452 of IMD 480 such that distal end 487 of posts 486 are available for permanent connection to ends 469 of elements 467 of lead 463 (FIG. 14B). In some examples, such permanent connection may be implemented via fasteners (e.g. crimp tube) and/or direct welding using techniques including resistance welding, laser welding, etc.

As in at least some examples associated with IMD 470 of FIG. 14C, after welding a connection the posts 486 and elements 467 may be encapsulated in an electrically non-conductive material. It will be understood that proximal end of posts 486 not visible in FIG. 14E are permanently connected to circuitry 59 within circuitry element 452 in FIG. 14E.

In some examples, the lead 452 of the device 440 in FIG. 14A is removably couplable relative to circuitry element 52. In some examples, the proximal portion 456 of lead 452 is removably insertable into a slot 472 of circuitry element 52, as shown in diagram 490 of FIG. 15A.

Figure 15A:
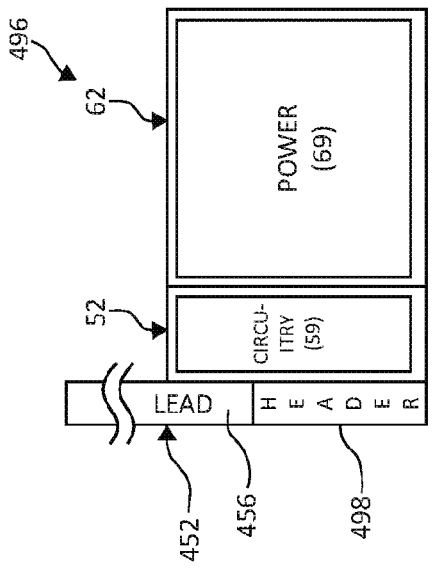
FIG. 15A is a partial side view schematically representing removable connection of a lead relative to a housing of a circuitry element, according to an example of the present disclosure.
Figure 15B:
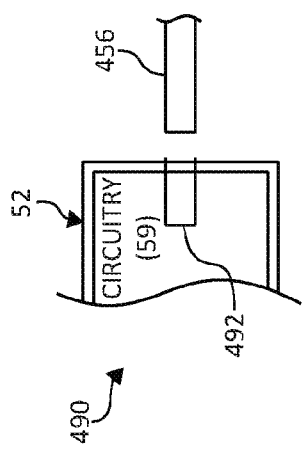
FIG. 15B is a block diagram schematically representing an implantable medical device, according to an example of the present disclosure.

FIG. 15B is block diagram schematically representing an implantable medical device 496 in which removable connection of the proximal portion 456 of lead 452 is made via a header 498 in communication with circuitry element 52, and with power element 62 operably coupled relative to circuitry element 52. In some examples, the header 498 can removably receive the proximal portion 456 of lead 452 and thereby electrically and mechanically connect the lead 452 (and the at least one source stimulation electrode 314) relative to the circuitry 59 within circuitry element 52. However, in other respects, the implantable medical device 496 may comprise at least some of substantially the same features and attributes as one or more of the various example implantable medical devices as previously described in association with at least FIGS. 1-13.

Figure 15C:
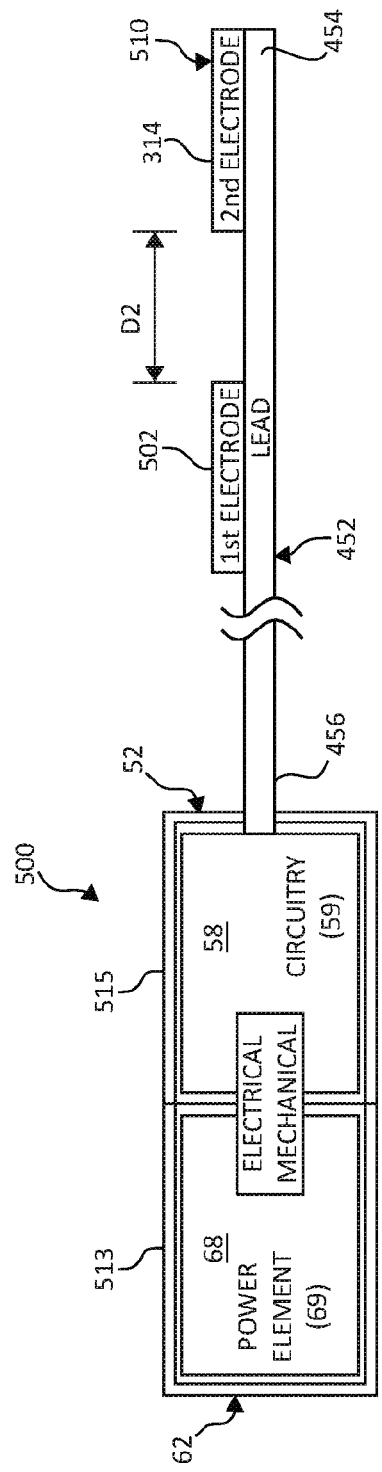
FIG. 15C is a block diagram schematically representing an implantable medical device including a lead, according to an example of the present disclosure.

FIG. 15C is a block diagram schematically representing an implantable medical device 500, according to one example of the present disclosure. In some examples, implantable medical device 500 comprises at least some of substantially the same features and attributes as implantable medical device 440 of FIG. 14A (and/or FIGS. 14B-14D), except with a first electrode 502 located on lead 452 instead of on a housing of one of the respective circuitry and power elements 52, 62 as in FIG. 14A. In addition, in some examples associated with FIG. 15C, the circuitry element 52 and power element 62 are electrically isolated from tissue via a non-conductive coating or surface 513, 515 for each of respective power element 62 and circuitry element 52, as shown in FIG. 15C. Via this arrangement, in some examples and as further shown in FIG. 15C, via a spacing D2 allowing some tissue to be located between first electrode 502 and second electrode 314, the stimulation electrode array 510 may be operated in a bipolar stimulation mode. In some examples, the second electrode 314 comprises a source stimulation electrode while the first electrode 502 comprises a return stimulation electrode. In some examples, second electrode 314 is located at a distal end portion 454 of the lead 452 while the first electrode 502 is spaced apart by a distance D2 to be located adjacent a proximal end portion 456 of the lead 452. However, in some examples, the first electrode 502 is also located at the distal end portion 454 of the lead 452 to be in relatively close proximity to, but spaced apart (D2) from, the second electrode 314.

With regard to at least some of the examples associated with FIGS. 1-15C, given the significant time, cost, and general undesirability associated with removing leads due to at least the invasiveness of such procedures, at least some examples of the present disclosure enhance long term patient health and goodwill regarding maintenance and/or upgrading of implantable components, such as a power element which can be removed and replaced without disturbing at least some implanted leads. It will be further understood that in some examples, the removable and replaceable element may comprise a circuitry element instead of a power element. In some examples, either or both of such power elements and circuitry elements may be removed and replaced without disturbing implanted leads.

FIG. 16 is an isometric view schematically representing an implantable medical device (IMD) 530, according to one example of the present disclosure. In some examples, IMD 530 comprises at least some of substantially the same features and attributes as the implantable medical devices and related components and relationships, as previously described in association with at least FIGS. 1-15C.

As shown in FIG. 16, IMD 530 comprises a first element 532 and a second element 542. In some examples, first element 532 may correspond to circuitry element 52 (FIGS. 1-15C) while second element 542 may correspond to power element 62 (FIG. 1-15C).

As shown in FIG. 16, first element 532 comprises a housing 536 including an external surface 537 and sealingly containing circuitry components (not shown). Second element 542 comprises a housing 546 including an external surface 547 and sealingly containing power components (not shown). A first coupling element 550 includes a first portion 552 and a second portion 554, with first portion 552 disposed on an end 548A of second element 542 and second portion 554 disposed on an end 538A of first element 532. The first portion 552 is removably insertable into and through the second portion 554, as represented by directional arrow A. At least an outer surface of the first portion 552 comprises an electrically conductive material to electrically conduct power (via second portion 554 of coupling element 550) into circuitry within first element 532. While first portion 552 can take a variety of shapes, in some examples the first portion 552 comprises a generally cylindrical shape or disc shape.

As shown in FIG. 17, in some examples the second portion 554 of first coupling element 550 comprises an annular ring having an outer portion 580 and an inner portion 582 sized and shaped to slidably receive first portion 552 of first coupling element 550 such that an outer surface of first portion 552 slidably engages the inner portion 582 of second portion 554 to establish both an electrical and mechanical connection.

In some examples, inner portion 582 of second portion 554 comprises a ring-shaped electrically coil 586 retained within an annular channel 587 and which is configured to pressingly engage the external surface of first portion 552 to thereby establish the removable, slidable electrical and mechanical connection of components (e.g. circuitry) within first element 532 relative to components (e.g. power) within second element 542. In one aspect, inner portion 582 of second portion 554 defines lumen 584.

In some examples, second portion 554 may be implemented via a contact available from Bal Seal Engineering, Inc. of Foothill Ranch, Calif.

In some examples, the first and second portions 552, 554 of first coupling element 550 are centrally located such that the first and second portions 552, 554 are concentrically nested relative to the threaded portions 570, 572 of a second coupling element 571, which are located an outer circumferential portion (e.g. periphery) of the housings 536, 546 of the first and second elements 532, 542.

With further reference to FIGS. 16-17, it will be understood that in some examples, the first element 532 may correspond to power element 62 while second element 542 may correspond to circuitry element 52.

In some examples, an additional securing mechanism is provided on at least one of the first and second elements 532, 542 to ensure that the first and second elements 532, 542 remain secured together. In some examples, the additional securing mechanism may take the form of an internally threaded collar 563 on the first element 532 and an associated set screw 565 selectively insertable relative to the collar 563 and engageable relative to the collar 563, with the collar 563 positioned and configured to permit an end of the set screw 565 to selectively engage a portion of the second element 542. It will be understood that a wide variety of fastening mechanisms can be used instead of, or with, a collar 563 and set screw 565 to implement selectively securing (e.g. at least mechanically) the first element 532 relative to the second element 542.

In some examples, the collar 563 is omitted and internal threads are provided within an aperture defined within a wall of the housing 536 of first element 532 with set screw 565 being selectively insertable and engageable relative to such internal threads.

FIGS. 18-24 provides examples of different modes of stimulation to implement a non-floating power architecture, such as in at least some examples when an outer wall of the housing of a power element sealingly contains power components and is directly exposable to bodily tissues. At least some of these examples stand in sharp contrast to some commercially available pulse generators (i.e. implantable neurostimulators) in which a case of the pulse generator envelopes or encapsulates circuitry and a case or housing of a battery is contained by the case of the pulse generator.

FIG. 18 is a flow diagram schematically representing a method 600 of voltage mode stimulation, according to one example of the present disclosure. In some examples, method 600 may be implemented via at least some of the substantially features and attributes as described in association with at least FIGS. 22-29 and also FIGS. 1-17. In some examples, method 600 may be implemented via at least some features and attributes other than those described in association with at least FIGS. 22-29 and FIGS. 1-17.

As shown at 602 in FIG. 18, method 600 of voltage mode stimulation comprises implementing a stimulation phase via applying a first polarity voltage between a source stimulation electrode and a return stimulation electrode while at 604, method 600 comprises implementing a recharge phase via applying a second opposite polarity voltage between the source stimulation electrode and the return stimulation electrode. In some examples, the first polarity voltage is a negative voltage and the second opposite polarity voltage is a positive voltage. As shown at 606, this sequenced application of these stimulation phases and recharge phases is repeated, thereby providing charge-balanced stimulation to the nerve with a non-floating power architecture.

FIG. 19 is a flow diagram schematically representing aspects associated with a method 620 of stimulation, according to one example of the present disclosure. In some examples, method 620 may be implemented via at least some of the substantially features and attributes as described in association with at least FIGS. 22-29 and also FIGS. 1-17. In some examples, method 620 may be implemented via at least some features and attributes other than those described in association with at least FIGS. 22-29 and FIGS. 1-17. As shown at 622, in some examples the stimulation phase is implemented via selectively using (e.g. connecting) a first polarity power supply to charge a first capacitor (e.g. a Stimulation Phase capacitor), and then selectively discharging the first capacitor to a source stimulation output to apply a stimulation phase to the nerve.

As shown at 624, the recharge phase is implemented via selectively using (e.g. connecting) a second opposite polarity power supply to charge a second capacitor (e.g. Recharge Phase capacitor), and then selectively discharging the charged second capacitor to the source stimulation output to apply a return phase to the nerve. In some examples, the first polarity power supply is a negative power supply and the second opposite polarity power supply is a positive power supply.

In some examples, the recharge phase is applied via a voltage (second opposite polarity) less than a voltage (first polarity) by which the stimulation phase is applied, with the recharge phase have a longer duration than the stimulation phase. In this way, the total power consumed from the power element may be reduced while facilitating avoidance of exciting structures at the return stimulation electrode.

FIG. 20 is a flow diagram schematically representing a method 650 of current mode stimulation, according to one example of the present disclosure. In some examples, method 650 may be implemented via at least some of the substantially features and attributes as described in association with at least FIG. 24, and at least FIGS. 1-17 and 24-29. In some examples, method 650 may be implemented via at least some features and attributes other than those described in association with at least FIGS. 24-29 and FIGS. 1-17.

As shown at 652 of method 650 of current mode stimulation, a stimulation phase may be implemented via applying a first polarity current between a source stimulation electrode and a return stimulation electrode and at 654, a recharge phase may be implemented via applying a second opposite polarity current between the source stimulation electrode and the return stimulation electrode. In some examples, the first polarity current is a negative current and the second opposite polarity is a positive current. As shown at 656, this sequenced application of the stimulation phase and the recharge phase is repeated to provide charge-balanced stimulation to the nerve.

In some examples, the recharge phase is applied via a current (second opposite polarity) less than a current (first polarity) by which the stimulation phase is applied, with the recharge phase have a longer duration than the stimulation phase. In this way, the total power consumed from the power element may be reduced while facilitating avoidance of exciting structures at the return stimulation electrode.

FIG. 21 is a flow diagram schematically representing aspects associated with a method 670 of stimulation, according to one example of the present disclosure. In some examples, method 670 may be implemented via at least some of the substantially features and attributes as described in association with at least FIGS. 1-17 and 24-29. In some examples, method 670 may be implemented via at least some features and attributes other than those described in association with at least FIGS. 24-29 and FIGS. 1-17. As shown at 672, the stimulation phase may be implemented via selectively connecting a first polarity current source relative to a source stimulation output while at 674, the recharge phase may be implemented via selectively connecting a second opposite polarity current source relative to the source stimulation output.

Figure 22:
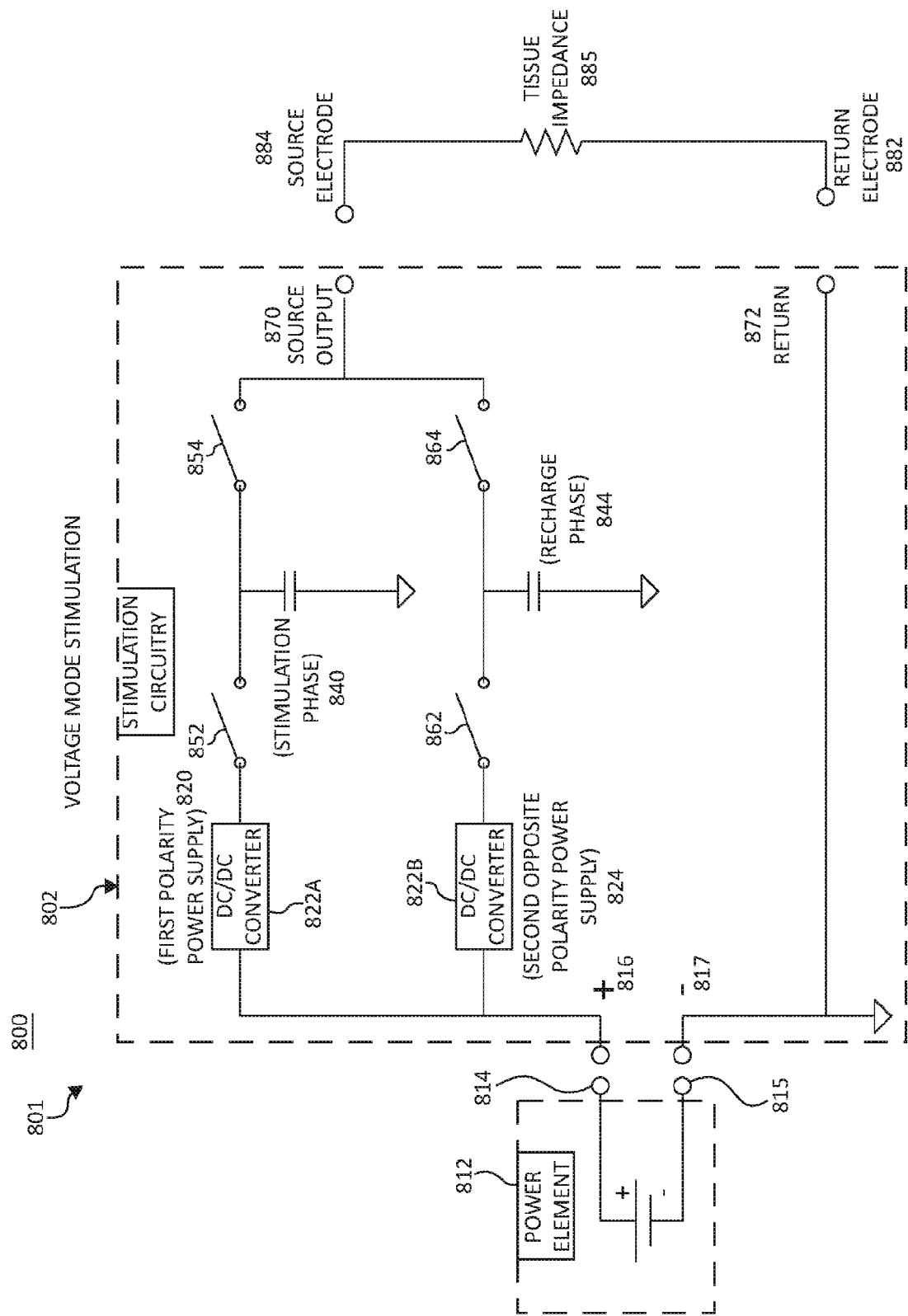
FIG. 22 is circuit diagram schematically representing a circuitry element for voltage mode stimulation in association with a power element, according to one example of the present disclosure.

FIG. 22 is circuit diagram 800 schematically representing at least some aspects of an implantable medical device (IMD) 801 including circuitry 802 for voltage mode stimulation in association with a power element 812, according to one example of the present disclosure. In some examples, circuitry 802 comprises one example implementation by which method 600, 620 in FIGS. 18-19 may be performed, and by which stimulation in association with at least FIGS. 1-17 and 25A-29 may be implemented. In some examples, circuitry 802 comprises one example implementation of at least a portion of a circuitry element (e.g. circuitry element 52).

As shown in FIG. 22, circuitry 802 comprises a positive voltage input 816 and a negative voltage input 817, a pair of DC/DC converters 822A, 822B, a stimulation phase capacitor 840, a recharge phase capacitor 844, a source output node 870, and a return node 872. The source output node 870 is connectable to source electrode 884 and the return node 872 is connectable to return electrode 882.

A power element 812 includes a positive output 814 connectable to the positive power input 816 and a negative output 815 connectable to the negative power input 817 of circuitry 802. As shown in FIG. 22, in some examples the power element 812 is removably connectable to circuitry 802.

In some examples, DC/DC converter 822A may act as a first polarity power supply 820, which becomes operably coupled during a stimulation phase to stimulation phase capacitor 840 via switch 852 to charge capacitor 840. After opening switch 852, switch 854 is closed to enable discharge of capacitor 840 to source stimulation output 870. In some examples, DC/DC converter 822B may act as a second opposite polarity power supply 824, which becomes operably coupled during a recharge phase to charge a recharge phase capacitor 844 via switch 862. After opening switch 862, switch 864 is closed to enable discharge of capacitor 844 to source stimulation output 870. In some examples, the first polarity power supply 820 is a negative power supply and the second opposite polarity power supply 822 is a positive power supply.

Figure 23A:
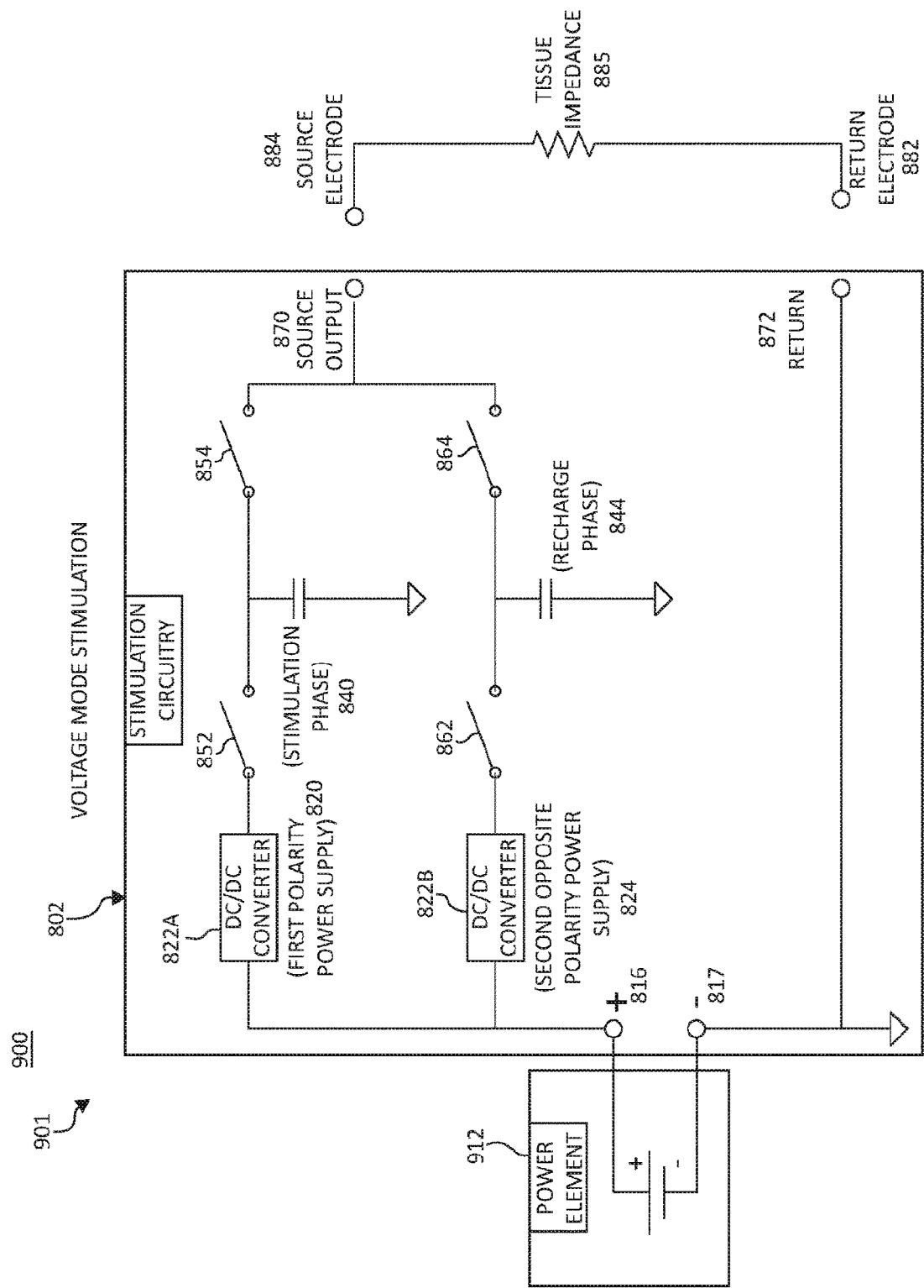
FIG. 23A is circuit diagram schematically representing a circuitry element for voltage mode stimulation in association with a power element, according to one example of the present disclosure.

FIG. 23A is circuit diagram 900 schematically representing at least some aspects of an implantable medical device IMD 901 including circuitry 802 for voltage mode stimulation in association with a power element 912, according to one example of the present disclosure. IMD 901 comprises substantially the same features and attributes as IMD 801, except with power element 912 being permanently connected relative to a circuit element including circuitry 802. In other words, in such examples, the power element 912 is not replaceable.

Figure 23B:
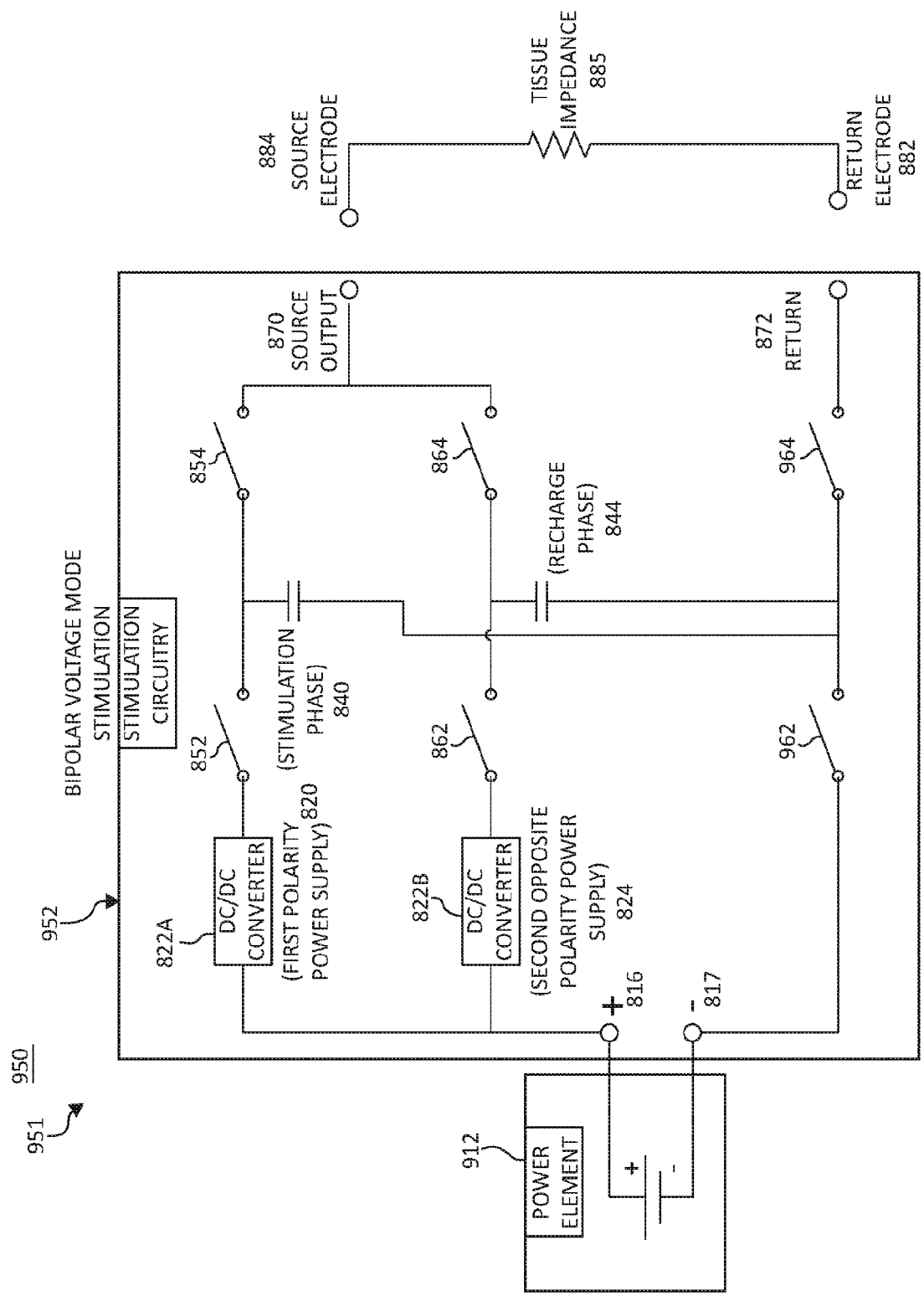
FIG. 23B is circuit diagram schematically representing a circuitry element for voltage mode stimulation in association with a power element, according to one example of the present disclosure.

FIG. 23B is a circuit diagram 950 schematically representing at least some aspects of an implantable medical device (IMD) 951 including circuitry 952 for voltage mode stimulation in association with a power element 912, according to one example of the present disclosure. IMD 951 comprises substantially the same features and attributes as IMD 901 of FIG. 23A (including circuitry 802), except with the introduction of switch 962 and switch 964, and with a housing of power element 912 not being electrically isolated from surrounding tissue. Via such arrangement, in at least some examples, a bipolar voltage mode of stimulation may be implemented even in arrangements in which an external surface of the housing of the power element is not electrically isolated from surrounding tissues (in which the power element is implanted).

In some examples, the arrangement of additional switches 962, 964 and non-electrical-isolation of power element 912 from tissue may be incorporated in IMD 800 of FIG. 22 in a manner similar to that shown and described in FIG. 23A.

In some examples, in operation of circuitry 952, switch 962 is closed (i.e. turned on) during charging of the stimulation phase capacitor 840 and of the recharge phase capacitor 844, and then otherwise generally open. Meanwhile, switch 964 is closed (i.e. turned on) when delivering the stimulation phase and recharge phase (via discharge of capacitors 840, 844), and then otherwise generally open.

Via this arrangement, in some examples both of the source stimulation electrode(s) 884 and the return stimulation electrode(s) 882 of a stimulation array are located on a lead, such as but not limited to, a distal end of a lead locatable adjacent a body tissue (e.g. nerve or muscle) to be stimulated. In some examples, such a lead may have at least some of substantially the same features and attributes as lead 952 in FIG. 15C including first electrode 502 and second electrode 314. In some such arrangements, a conductive external surface of a housing (e.g. case) of the power element 912 is not electrically isolated from the surrounding tissue (in which it is located/implanted). However, because in at least some examples of this arrangement, no current flows to an external conductive surface of a housing of the power element 912, the power element 912 may be considered electrically inactive relative to at least the source stimulation electrode(s) 884 and the return stimulation electrode(s) 882 regarding application of an electrical stimulation signal.

In some examples, the source electrode(s) 884 and the return electrode(s) 882 are located on a housing of the circuitry element of the implantable medical device with the source electrode(s) 884 and the return electrode(s) 882 being electrically insulated from any conductive portion(s) of the external surface of such housing. In some such examples, no lead is present or if the lead is present, the lead does not carry the source electrode(s) 884 and the return electrode(s) 882.

In some examples, some source electrode(s) 884 are located on a lead while some source electrode(s) 884 are located on a housing of the circuitry element of the implantable medical device, and some return stimulation electrode(s) 882 are located on a lead while some return stimulation electrode(s) 882 are located on a housing of the circuitry element of the implantable medical device. In such examples, the source electrode(s) 884 and the return electrode(s) 882 on such housing are electrically insulated from any conductive portion(s) of the external surface of such housing.

Figure 24:
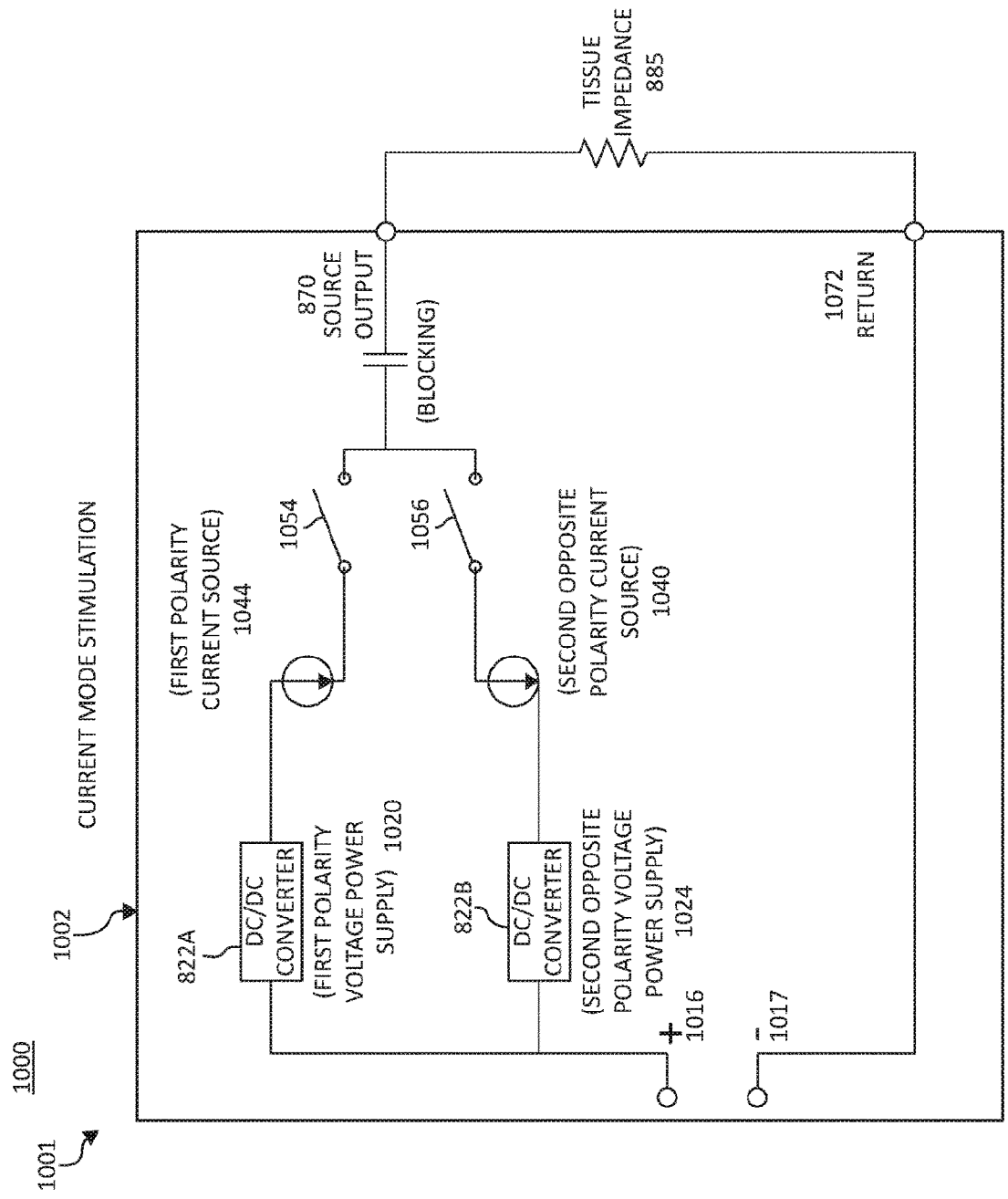
FIG. 24 is circuit diagram schematically representing a circuitry element for current mode stimulation in association with a power element, according to one example of the present disclosure.

FIG. 24 is circuit diagram 1000 schematically representing at least some aspects of an implantable medical device IMD 1001 including circuitry 1002 for current mode stimulation in association with a power element, according to one example of the present disclosure. In some examples, the power element may be implemented as a removably connectable power element (e.g. 812 in FIG. 22) or as a permanently connected power element (e.g. 912 in FIGS. 23A, 23B). Either of such power elements may be connected to the respective positive power input 1016 and negative power input 1017, as shown in FIG. 24.

As shown in FIG. 24, circuitry 1002 comprises a positive voltage input 1016 and a negative voltage input 1017, a pair of DC/DC converters 822A, 822B, a stimulation phase capacitor 1040, a recharge phase current source 1044, a source output node 1070, and a return node 1072. The source output node 1070 is connectable to source stimulation electrode 884 and the return node 1072 is connectable to return stimulation electrode 882.

In some examples, DC/DC converter 822A may act as a first polarity power supply 1020, which is connected to recharge phase current source 1044, which in turn becomes connectable to source stimulation output 870 via switch 1054 and blocking capacitor 1065. DC/DC converter 822B may act as a second opposite polarity power supply 1024, which is connected to stimulation phase current source 1040, which in turn becomes connectable to source output 870 via switch 1056 and blocking capacitor 1065.

In some examples, the blocking capacitor 1065 acts as a safeguard by preventing any excess charge from reaching bodily tissues in the case of dysfunction of source switches 1054, 1056. In some examples, the voltage produced by the DC/DC converter 822A, 822B is of an amplitude to maintain adequate voltage at the respective current sources 1040, 1044, which is equal to or larger than the voltage differential across the tissue impedance 885 caused by the stimulation current.

Figure 25A:
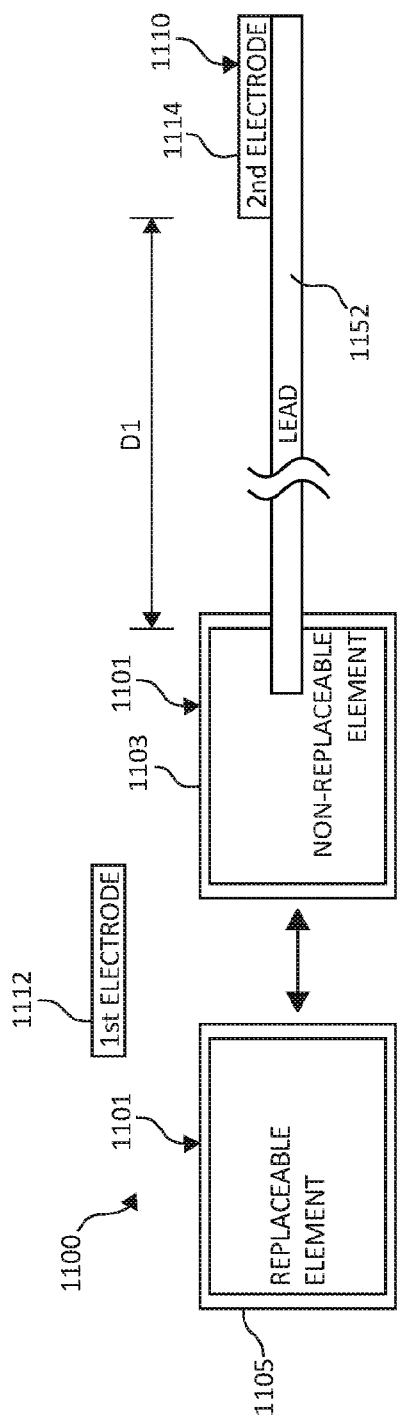
FIG. 25A is a block diagram schematically representing an implantable medical device including a stimulation electrode array arranged relative to a lead and a pulse generator including a replaceable element, according to one example of the present disclosure.

FIG. 25A is a block diagram schematically representing an implantable medical device (IMD) 1100 including a stimulation electrode array arranged relative to a lead and a pulse generator including a replaceable element, according to one example of the present disclosure. In some examples, IMD 1100 comprises at least some of substantially the same features and attributes as previously described in association with at least FIGS. 1-24.

As shown in FIG. 25A, IMD 1100 comprises a pulse generator 1101 comprising a non-replaceable element 1103 and a replaceable element 1105 removably connectable to the non-replaceable element 1103. The non-replaceable element 1103 is sealingly contained and the replaceable element 1105 is sealingly contained separately from the sealingly contained non-replaceable element 1103. The replaceable element 1105 and the non-replaceable element 1103 are selectively operably coupled together, such as (but not limited to) being removably connectable electrically and mechanically relative to each other.

As further shown in FIG. 25A, a stimulation electrode array 1110 comprises at least one second electrode 1114 and a first electrode 1112 (e.g. a return electrode) associated with a housing of at least one of the replaceable element 1105 and the non-replaceable element 1103. In some examples, the IMD 1100 comprises a lead 1152, which extends from and is permanently connected to the non-replaceable element 1103. In some examples, the manner of permanent connection comprises at least some of substantially the same features and attributes as any one (or a combination of) the permanent connection methods as previously described in association with at least FIGS. 14A-14E.

In some examples, the at least one second electrode 1114 is located on a portion of the lead 1152 to be spaced apart from the first electrode 1112 by a distance D1, wherein first electrode 1112 may be located on a housing of the replaceable element 1105 or of the non-replaceable element 1103. In some examples, the at least one second electrode 1114 may be located on a distal end portion of the lead 1152.

In some examples, the replaceable element 1105 comprises a power element (e.g. 62) and the non-replaceable element 1103 comprises a circuitry element (e.g. 52), such as stimulation circuitry. However, in some examples, the replaceable element 1105 comprises a circuitry element (e.g. 52) and the non-replaceable element 1103 comprises a power element (e.g. 62).

Figure 25B:
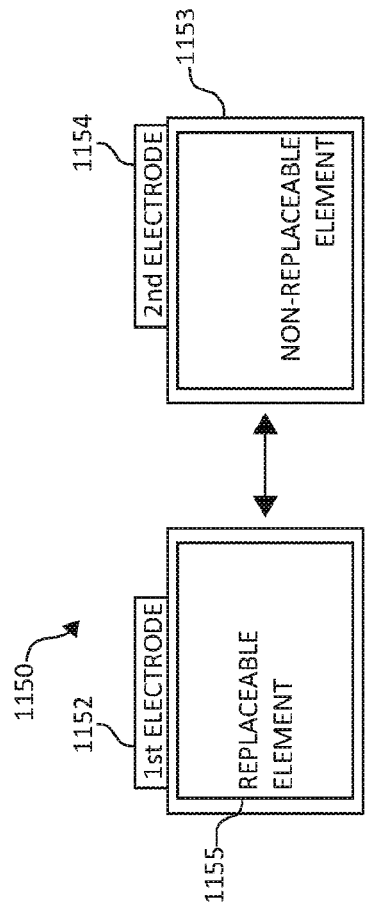
FIG. 25B is a block diagram schematically representing an implantable medical device omitting a lead while including a stimulation electrode array arranged relative to a pulse generator including a replaceable element and a non-replaceable element, according to one example of the present disclosure.

FIG. 25B is a block diagram schematically representing an implantable medical device (IMD) 1150 including a stimulation electrode array, according to one example of the present disclosure. In some examples, IMD 1150 comprises at least some of substantially the same features and attributes as previously described in association with at least FIG. 25A, except omitting a lead. In some examples, a first electrode 1152 is located on a replaceable element 1155 and a second electrode 1154 is located a non-replaceable element 1153. In some examples, first electrode 1152 is located on non-replaceable element 1153 while second electrode 1154 is located on replaceable element 1153.

As in some of the examples associated with FIG. 25A, the first electrode 1152 comprises a return stimulation electrode while the second electrode 1154 comprises at least one source stimulation electrode, or vice versa. As in some of the examples associated with FIG. 25A, the replaceable element 1155 comprises a power element (e.g. 62 in FIG. 1) while the non-replaceable element 1153 comprises a circuitry element (e.g. 52 in FIG. 1), or vice versa.

With respect to the examples of FIGS. 25A-25B, in some examples at least one of the respective replaceable and non-replaceable elements 1105, 1103 may comprise both a power component and a circuitry component sealingly contained within a single housing. In such arrangements, at least some of the circuitry of an implantable neurostimulator is distributed between the respective replaceable and non-replaceable elements 1105, 1103.

FIG. 26 is a flow diagram schematically representing a method 1200, according to one example of the present disclosure. In some examples, method 1200 is performed via at least some of substantially the same features and attributes as previously described in association with at least FIG. 25, in association with at least FIGS. 1-24, and/or in association with at least FIGS. 27-29.

As shown at 1202 in FIG. 26, method 1200 comprises implanting in a first surgical procedure an implantable medical device having a replaceable element and a non-replaceable element. In some examples, a lead extends from the non-replaceable element. At 1204, after a first period of time, in a second surgical procedure the replaceable element is separated from the non-replaceable element and removed from the patient's body while retaining (i.e. not removing) the non-replaceable element and the lead. A new (e.g. second) replaceable element is implanted and removably connected to the non-replaceable element.

A wide variety of reasons or situations may drive the desire to replace an implantable element, such as the replaceable element (e.g. 1105, or 1103 in some examples). In one instance, the replaceable element 1105 may comprise a power element and at a later time after initial implantation, a decision has been made to replace the battery for a larger size, end of useful life, and/or other reasons. By making the power element a replaceable element, the power element may be replaced without removing the non-replaceable element, such as the circuitry element, and without disconnecting leads (supporting stimulation electrodes) from the circuitry element. Given the significant time, cost, and general undesirability associated with removing leads due to at least the invasiveness of such procedures, at least some examples of the present disclosure enhance long term patient health and goodwill via enabling removal and replacement of some elements of an implantable pulse generator. In some examples, the replaceable element comprises a power element, such as a battery. In some examples, the replaceable element may comprise some circuitry components. In some examples, the replaceable element may comprise both power and circuitry components. In some examples, replaceable element comprises a sensor element not present in the first replaceable element.

FIG. 27 is a block diagram schematically representing a control portion 1700, according to one example of the present disclosure. In some examples, control portion 1700 includes a controller 1702 and a memory 1704. In some examples, control portion 1700 provides one example implementation of a control portion forming a part of and/or implementing the implantable medical devices and methods as represented throughout the present disclosure in association with FIGS. 1-26.

In general terms, controller 1702 of control portion 1700 comprises at least one processor 1703 and associated memories. The controller 1702 is electrically couplable to, and in communication with, memory 1704 to generate control signals to direct operation of at least some components of the devices, elements, components, functions, methods, etc. described throughout the present disclosure. In some examples, these generated control signals include, but are not limited to, employing manager 1705 stored in memory 1704 to manage therapy for sleep disordered breathing, including but not limited to applying nerve stimulation, in the manner described in at least some examples of the present disclosure. In some examples, such generated control signals may at least partially control operation of the voltage mode and/or current modes of stimulation and associated circuitry components. It will be further understood that control portion 1700 (or another control portion) may also be employed to operate general functions of the various devices and/or components thereof described throughout the various examples of the present disclosure.

In response to or based upon commands received via a user interface (e.g. user interface 1710 in FIG. 28) and/or via machine readable instructions, controller 1702 generates control signals to implement therapy (including but not limited to nerve stimulation) and/or circuitry control in accordance with at least some of the previously described examples of the present disclosure. In some examples, controller 1702 is embodied in a general purpose computing device while in some examples, controller 1702 is incorporated into or associated with at least some of the associated components of the devices as described throughout the present disclosure.

For purposes of this application, in reference to the controller 1702, the term "processor" shall mean a presently developed or future developed processor (or processing resources) that executes sequences of machine readable instructions contained in a memory. In some examples, execution of the sequences of machine readable instructions, such as those provided via memory 1704 of control portion 1700 cause the processor to perform actions, such as operating controller 1702 to implement sleep disordered breathing (SDB) therapy (including but not limited to nerve stimulation), as generally described in (or consistent with) at least some examples of the present disclosure. The machine readable instructions may be loaded in a random access memory (RAM) for execution by the processor from their stored location in a read only memory (ROM), a mass storage device, or some other persistent storage (e.g., non-transitory tangible medium or non-volatile tangible medium, as represented by memory 1704. In some examples, memory 1704 comprises a computer readable tangible medium providing non-volatile storage of the machine readable instructions executable by a process of controller 1702. In some examples, hard wired circuitry may be used in place of or in combination with machine readable instructions to implement the functions described. For example, controller 1702 may be embodied as part of at least one application-specific integrated circuit (ASIC). In at least some examples, the controller 1702 is not limited to any specific combination of hardware circuitry and machine readable instructions, nor limited to any particular source for the machine readable instructions executed by the controller 1702.

FIG. 28 is a block diagram schematically representing user interface 1710, according to one example of the present disclosure. In some examples, user interface 1710 forms part or and/or is accessible via a device external to the patient and by which the implantable medical device (or portions thereof) may be at least partially controlled and/or monitored.

In some examples, user interface 1710 comprises a user interface or other display that provides for the simultaneous display, activation, and/or operation of features and attributes of an implantable medical device. In some examples, at least some portions or aspects of the user interface 1710 are provided via a graphical user interface (GUI). In some examples, as shown in FIG. 28, user interface 1710 includes display 1712 and input 1714.

Figure 29:
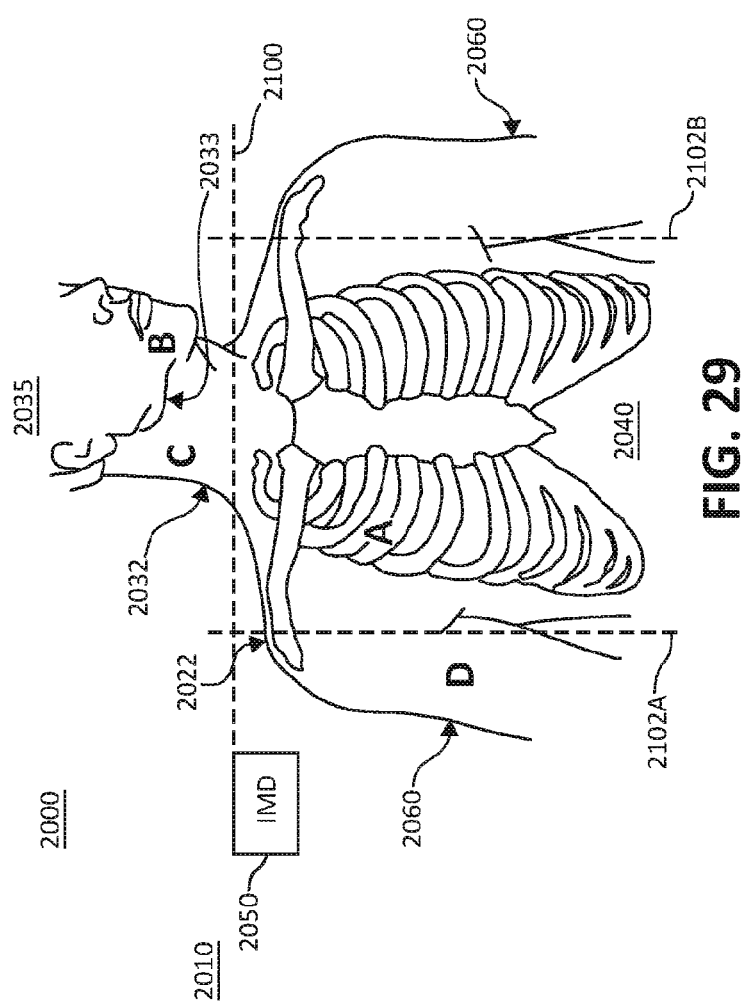
FIG. 29 is a diagram schematically representing a patient's body in association with methods of therapy, stimulation, implantation, and the like via an implantable medical device, according to one example of the present disclosure.

While the example implantable medical devices of the present disclosure may take a wide variety of forms and may be deployed in a wide variety of different portions of a patient's body, in some examples an implantable medical device (e.g. at least 50 of FIG. 1) may deployed in at least some of the example arrangements shown in FIG. 29. FIG. 29 is a schematic diagram 2000 of an at least partially implantable stimulation system 2010, according to an example of the present disclosure, which comprises implantable medical device 2050, which in turn comprises at least some of substantially the same features and attributes as one or more of the previously described example implantable medical devices in association with FIGS. 1-28. In general terms, in such examples the implantable medical device 2050 of FIG. 29 forms part of a stimulation system 2010 to deliver stimulation, and therefore may sometimes be referred to as an implantable neurostimulator, implantable neurostimulator device, implantable pulse generator (IPG), and the like. In some examples, the stimulation is delivered to a nerve to cause a response in a corresponding innervated muscle. In some examples, the nerve may be related to restoring upper airway patency, such as when the implantable medical device (IMD) 2050 is used in a method of treating sleep disordered breathing, which includes but is not limited to a method of therapy (e.g. treatment) for obstructive sleep apnea. In some examples, the nerve comprises a hypoglossal nerve 2033 and/or other upper-airway-patency-related nerve. In some examples, the stimulation may be delivered directly to a muscle.

As shown in FIG. 29, various locations A, B, C, and/or D are identified at which a method of therapy, method of stimulation, method of monitoring, method of implantation, etc. may be performed in association with an implantable medical device (IMD) 2050.

For instance, in some examples IMD 2050 may be implanted (e.g. subcutaneously) as represented via indicator C within a neck region 32. In some instances, the IMD 2050 may comprise electrodes on the surface of the housing of the IMD 2050 such that stimulation may be applied to a target nerve and/or target muscle without use of a stimulation lead, such as via the examples previously described in association with at least FIGS. 8-13. In some instances, such example implementations associated with an IMD 2050 may sometimes be referred to as a leadless implantable stimulation device or system. Accordingly, at least some example implementations of IMD 2050 may be sized and/or shaped for implantation within a single body region. However, it will be understood that such leadless stimulation devices may be implemented in many different regions of the patient's entire body. In one aspect, such leadless implantable devices may ease implantation because a single incision and/or percutaneous access may be used for delivery due to a reduced size and/or favorable shape of the leadless implantable medical device, which may significantly expedite deployment, reduce complexities, save time and money, etc.

To the extent that an example IMD 2050 is sized and/or shaped for implantation in locations of a patient's body which are not conducive to implantation of more traditionally-sized implantable pulse generators, such as pacemakers, etc., such IMDs 2050 may sometimes be referred to with the term "microstimulator." However, the use of the term "microstimulator" does not limit or prevent implantation of the IMD 2050 in various locations (e.g. A) in larger portions 2040 of the patient's body, such as the chest, torso, etc.

In some examples, an implanted IMD 2050 may be coupled to a stimulation lead, such as described via at least the examples associated with at least FIGS. 14A-15C. In some such examples, the lead may have a length (e.g. D1 in at least FIG. 14A) such that an associated stimulation electrode may be implanted at or near a nerve per indicator B in FIG. 29, such as nerve 2033, which is spaced apart from the IMD 2050 implanted lower in the neck region 2032 per indicator C. In some such examples, the IMD 2050 may be referred to as a microstimulator or microstimulator IMD 2050.

However, in some other example implementations, a stimulation lead may be coupled to IMD 2050 with the lead having a relatively short length (e.g. D1 in FIG. 14A) such that both the IMD 2050 and associated lead are implanted per indicator C within a single body region, such as neck region 32. The lead may then be coupled to a target nerve or target muscle in the single body region. It will be understood that such example implementations are not limited to the neck region but may occur at various locations throughout the entire body of the patient. In some such examples, the IMD 2050 alone, or the combination of the IMD 2050 and lead, may be referred to as a microstimulator or microstimulator IMD 2050.

In some examples, a stimulation lead may be coupled to IMD 2050 with the lead having a length (e.g. D1 in at least FIGS. 14A-15C) to extend from one body region to another body region, such as when the IMD 2050 is implanted at location A (e.g. pectoral) within one body region 2040 and the lead extends from the IMD 2050 for implantation into a different body region, such as implantation (D) in region 2060 or for implantation (C and/or B) in head/neck region 2032, 2035. As shown in FIG. 29, dashed lines 2100, 2102A, 2102B schematically represent example boundaries between at least some different regions of the patient's body.

Accordingly, it will be understood that among other features and attributes, the diagram in FIG. 20 at least schematically represents at least some example methods of therapy, methods of treatment, methods of implantation, methods of stimulation, etc. in which the various example implantable medical devices and associated elements as previously described in association with at least FIGS. 1-28 may be deployed.

Although specific examples have been illustrated and described herein, it will be appreciated by those of ordinary skill in the art that a variety of alternate and/or equivalent implementations may be substituted for the specific examples shown and described without departing from the scope of the present disclosure. This application is intended to cover any adaptations or variations of the specific examples discussed herein.

The invention claimed is:

1. An implantable medical device comprising:
a first element comprising a first housing portion to sealingly contain circuitry;
a second element comprising a second housing portion to sealingly contain a power element to supply power to the circuitry; and
a first coupling element comprising a first portion disposed on the second element and a second portion disposed on the first element,
wherein the first portion is removably insertable into the second portion, and
wherein the second portion comprises an annular ring comprising an outer portion and an inner portion sized and shaped to slidably receive the first portion such that an outer surface of the first portion slidably engages the inner portion of the second portion.

2. The implantable medical device of claim 1, wherein the circuitry comprises stimulation circuitry.

3. The implantable medical device of claim 2, wherein the stimulation circuitry is programmed to treat sleep disordered breathing.

4. The implantable medical device of claim 1, wherein the sealingly contained power element is sealingly contained separate from, and independent of, the sealingly contained circuitry.

5. The implantable medical device of claim 4, wherein the power element and the circuitry are sealingly contained together as at least part of a single sealed container.

6. The implantable medical device of claim 1, wherein the power element is at least mechanically connected via the first coupling element relative to the first housing portion.

7. The implantable medical device of claim 6, wherein the first housing portion is at least mechanically connectable to the second housing portion via the first coupling element, and wherein an exterior wall of the power element defines the second housing portion.

8. The implantable medical device of claim 7, wherein the exterior wall is directly exposable to tissue.

9. The implantable medical device of claim 7, wherein at least a portion of the exterior wall defines an electrode of a stimulation electrode array.

10. The implantable medical device of claim 1, wherein the first coupling element both electrically and mechanically connects the power element and the circuitry relative to each other.

11. The implantable medical device of claim 1, where the first portion is disposed on an end of the second element and the second portion is disposed on an end of the first element.

12. The implantable medical device of claim 1, wherein the first portion comprises a cylindrical shape or a disc shape.

13. The implantable medical device of claim 1, wherein the outer surface of the first portion slidably engages the inner portion of the second portion to establish an electrical and a mechanical connection.

14. The implantable medical device of claim 1, wherein the inner portion comprises a ring-shaped electrical coil retained within an annular channel and configured to pressingly engage the outer surface of the first portion.

15. The implantable medical device of claim 1, further comprising:
a second coupling element comprising a first threaded portion disposed on the second element and a second threaded portion disposed on the first element,
wherein the first threaded portion is removably connectable to the second threaded portion.

16. The implantable medical device of claim 15, wherein the first portion is concentrically nested relative to the first threaded portion and the second portion is concentrically nested relative to the second threaded portion.

17. The implantable medical device of claim 15, wherein the first threaded portion is located at an outer circumferential portion of the second housing and the second threaded portion is located at an outer circumferential portion of the first housing.

* * * * *